(12) United States Patent
Dale

(10) Patent No.: US 7,959,196 B2
(45) Date of Patent: Jun. 14, 2011

(54) DOOR LOCKING MECHANISM

(75) Inventor: James D. Dale, Nashua, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 12/258,823

(22) Filed: Oct. 27, 2008

(65) Prior Publication Data
US 2009/0115199 A1    May 7, 2009

Related U.S. Application Data

(63) Continuation of application No. 10/696,984, filed on Oct. 30, 2003, now abandoned.

(51) Int. Cl.
*E05C 19/00* (2006.01)
*B65D 45/32* (2006.01)

(52) U.S. Cl. ............ 292/303; 292/95; 292/256.65
(58) Field of Classification Search ........... 292/95, 292/303
See application file for complete search history.

(56) References Cited

U.S. PATENT DOCUMENTS

| | | | | |
|---|---|---|---|---|
| 1,133,254 A * | 3/1915 | Backus | ............ | 292/127 |
| 1,664,576 A * | 4/1928 | Stuart | ............ | 292/127 |
| 2,659,115 A * | 11/1953 | Anderson et al. | ............ | 49/277 |
| 2,776,854 A * | 1/1957 | Billstrom | ............ | 292/256 |
| 3,339,956 A * | 9/1967 | Bencene et al. | ............ | 292/127 |
| 3,481,076 A * | 12/1969 | Bedard | ............ | 49/279 |
| 3,620,215 A | 11/1971 | Tysk et al. | | |
| 3,823,724 A | 7/1974 | Davis | | |
| 3,946,731 A | 3/1976 | Lichtenstein | | |
| 4,073,521 A * | 2/1978 | Mena | ............ | 292/256.65 |
| 4,093,176 A * | 6/1978 | Contastin | ............ | 249/167 |
| 4,479,760 A | 10/1984 | Bilstad et al. | | |
| 4,613,327 A | 9/1986 | Tegrarian et al. | | |
| 4,634,430 A | 1/1987 | Polaschegg | | |
| 4,925,152 A | 5/1990 | Huber | | |
| 5,088,515 A | 2/1992 | Kamen | | |
| 5,150,796 A * | 9/1992 | Pierson | ............ | 209/370 |
| 5,186,333 A * | 2/1993 | Pierson et al. | ............ | 209/370 |
| 5,294,157 A * | 3/1994 | Smith et al. | ............ | 292/25 |

(Continued)

FOREIGN PATENT DOCUMENTS
EP     0319272    6/1989

OTHER PUBLICATIONS

Plaintiff's Trial Brief, *Baxter Healthcare Corp., Baxter Healthcare SA, and DEKA Products Limited Partnership* vs. *Fresenius Medical Care Holdings, Inc., d/b/a Fresenius Medical Care North America, and Fresenius USA, Inc.*, Civil Case No. C 07-01359 PJH (JL), U.S. Dist. Court for the Northern District of California, Document 359 filed Jan. 29, 2010.

(Continued)

*Primary Examiner* — Carlos Lugo
(74) *Attorney, Agent, or Firm* — Marc J. Gorayeb

(57) ABSTRACT

A system and method for locking a door. An assembly has a first engagement surface. A door is coupled to the assembly, the door including a latch member having a second engagement surface for engaging the first engagement surface. A movable member is capable of generating a force against at least one of the assembly and the door to press together and substantially prevent disengagement of the first engagement surface and the second engagement surface.

14 Claims, 26 Drawing Sheets

U.S. PATENT DOCUMENTS

| | | | |
|---|---|---|---|
| 5,324,422 | A | 6/1994 | Colleran et al. |
| 5,421,823 | A | 6/1995 | Kamen et al. |
| 5,431,626 | A | 7/1995 | Bryant et al. |
| 5,915,805 | A * | 6/1999 | Lee .............................. 312/405 |
| 5,988,709 | A * | 11/1999 | Lee et al. ..................... 292/199 |
| 6,814,547 | B2 | 11/2004 | Childers et al. |

OTHER PUBLICATIONS

Fresenius' Trial Brief, *Baxter Healthcare Corp., Baxter Healthcare SA, and DEKA Products Limited Partnership* vs. *Fresenius Medical Care Holdings, Inc.*, d/b/a Fresenius Medical Care North America, and Fresenius USA, Inc., Civil Case No. C 07-01359 PJH (JL) U.S. Dist. Court for the Northern District of California, Document 354 filed Jan. 29, 2010.

Plaintiff's Supplemental Brief Regarding "Pressure Conveying Element" and "Pressure Transfer Element," *Baxter Healthcare SA, and DEKA Products Limited Partnership* vs. *Fresenius Medical Care Holdings, Inc.*, d/b/a Fresenius Medical Care North America, and Fresenius USA, Inc., Civil Case No. C 07-01359 PJH (JL), U.S. Dist. Court for the Northern District of California, Document 393 filed Feb. 26, 2010.

Stipulation of Removal of Liberty Cycler Functionality Relating to, and Dismissal of, U.S. Patent No. 5,431,626, *Baxter Healthcare SA, and DEKA Products Limited Partnership* vs. *Fresenius Medical Care Holdings, Inc.*, d/b/a Fresenius Medical Care North America, and Fresenius USA, Inc., Civil Case No. C 07-01359 PJH (JL), U.S. Dist. Court for the Northern District of California, Document 398 filed Mar. 18, 2010.

Fig. 1: Undated photograph of UVAR™ XTS™ Photopheresis System Marketed by Therakos, Inc.

Fig. 2: Undated photograph of open compartments of UVAR™ XTS™ Photopheresis System marketed by Therakos, Inc., showing pumping cassette compartment and door in lower right portion of photograph.

Fig. 3: Undated photograph of pumping cassette of UVAR™ XTS™ Photopheresis System Marketed by Therakos, Inc.

Fig. 4: Manufacturing specification of the latching assembly of the pumping cassette compartment door of UVAR™ XTS™ Photopheresis System Marketed by Therakos, Inc., dated Nov. 5, 1999.

* cited by examiner

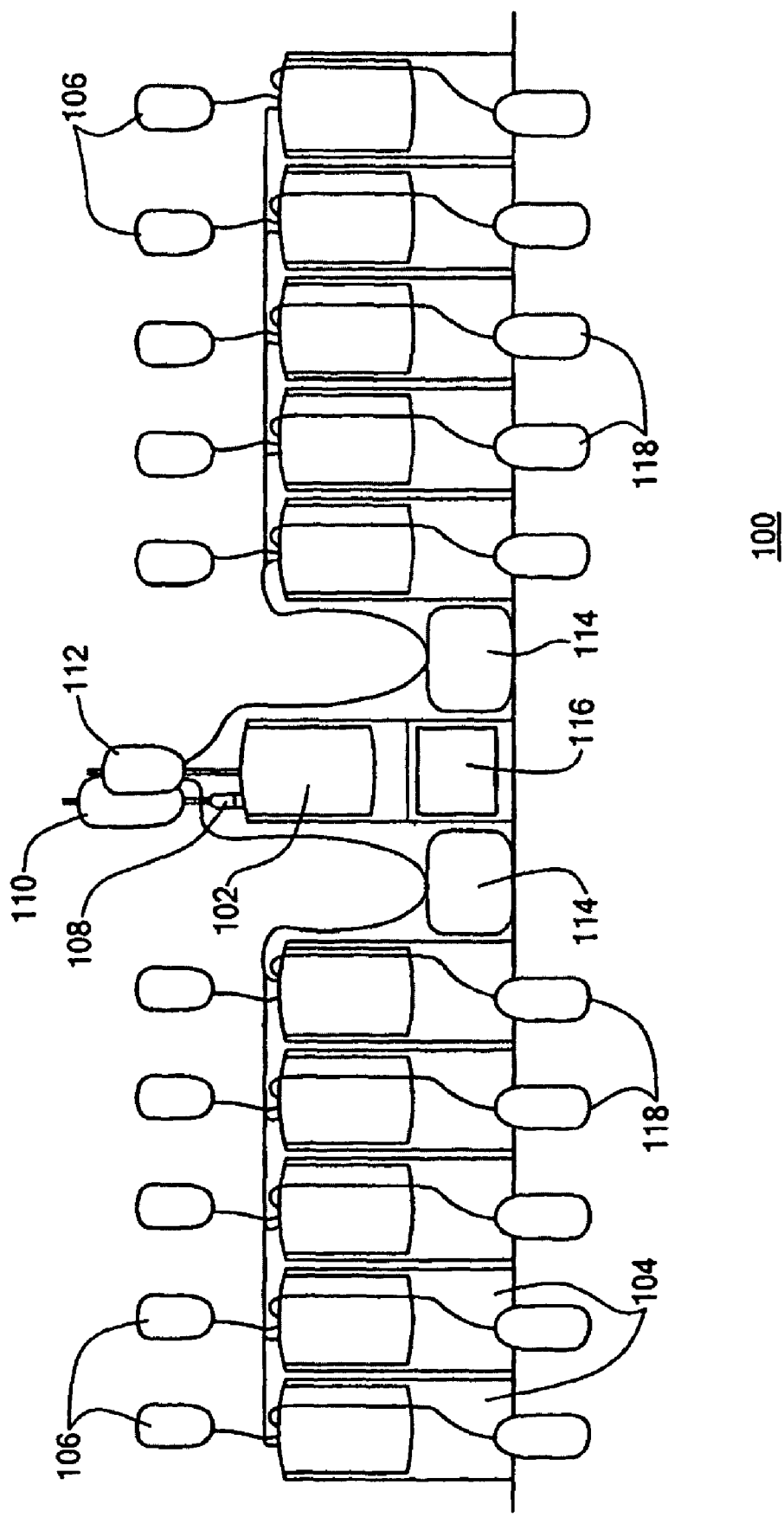

DOOR LOCKING MECHANISM

CROSS-REFERENCE TO RELATED APPLICATION(S)

The present application is a continuation of U.S. patent application Ser. No. 10/696,984 filed Oct. 30, 2003 and entitled DOOR LOCKING MECHANISM which application may include subject matter related to one or more of the following commonly-owned United States patent applications, each of which was filed on Oct. 30, 2003 and is hereby incorporated herein by reference in its entirety:
U.S. patent application Ser. No. 10/696,969 entitled SYSTEM, DEVICE, AND METHOD FOR MIXING A SUBSTANCE WITH A LIQUID (referred to herein as "Application D70") published as U.S. Publication No. US-2005-0095576 on May 5, 2005;
U.S. patent application Ser. No. 10/696,893 entitled SYSTEM, DEVICE, AND METHOD FOR MIXING LIQUIDS (referred to herein as "Application D71") published as U.S. Publication No. US-2005-0094485 on May 5, 2005;
U.S. patent application Ser. No. 10/696,818 entitled TWO-STAGE MIXING SYSTEM, APPARATUS, AND METHOD (referred to herein as "Application D72") now issued as U.S. Pat. No. 7,354,190 issued Apr. 8, 2008;
U.S. patent application Ser. No. 10/697,176 entitled SYSTEM AND METHOD FOR PUMPING FLUID USING A PUMP CASSETTE (referred to herein as "Application D73") published as U.S. Publication No. US-2005-0095141 on May 5, 2005;
U.S. patent application Ser. No. 10/697,450 entitled BEZEL ASSEMBLY FOR PNEUMATIC CONTROL (referred to herein as "Application D75") published as U.S. Publication No. US-2005-0095154 on May 5, 2005;
U.S. patent application Ser. No. 10/697,862 entitled PUMP CASSETTE WITH SPIKING ASSEMBLY (referred to herein as "Application D84") published as U.S. Publication No. US-2005-0096583; and
U.S. patent application Ser. No. 10/696,990 entitled PUMP CASSETTE BANK (referred to herein as "Application D85") published as U.S. Publication No. US-2005-0095153 on May 5, 2005.

FIELD OF THE INVENTION

The present invention relates generally to a door locking mechanism.

BACKGROUND OF THE INVENTION

Various door latch mechanisms for fastening a door to an assembly are known in the prior art. For examples a spring-loaded latch may protrude through the door and include a projection for engaging an undercut on the assembly. Upon pushing the door closed, the projection on the latch aligns with the undercut to prevent the door from being opened. Opening the door includes manipulating the handle such that the projection and undercut are no longer aligned, and then pulling on the door.

One disadvantage of such a latch is that an operator may inadvertently manipulate the handle causing the door to swing open. Another disadvantage is that an operator may purposely open the door when it should remain closed. For example, opening the door may pose a safety hazard to the operator, or allow various subjects to escape.

SUMMARY OF THE INVENTION

In accordance with one aspect of the invention, a door locking system includes an assembly having a first engagement surface. A door is coupled to the assembly. The door includes a latch member having a second engagement surface for engaging the first engagement surface. A movable member is capable of generating a force against at least one of the assembly and the door to press together and substantially prevent disengagement of the first engagement surface and the second engagement surface.

In accordance with related embodiments of the invention, the first engagement surface forms an undercut, and the second engagement surface forms a projection for engaging the undercut. The latch member may include a post extending from the door, the post including the second engagement surface. The latch member may include a handle for operating the latch. The handle may be capable of pivoting to control alignment of the second engagement surface. When the first engagement surface is engaged with the second engagement surface, the movable member generating force against the one of the door and the assembly may prevent the handle from pivoting. The movable member may be capable of generating a continuous force against the at least one of the assembly and the door. The movable member may be coupled to one of the door and the assembly and/or positioned between the door and a surface of the assembly. The movable member may contact the at least one of the assembly and the door. An element may be positioned between the movable member and the at least one of the assembly and the door, such as a pump cassette, wherein the movable member contacts the element when generating the force.

In accordance with further related embodiments of the invention, the movable member is an expandable member, such as a bladder. A pneumatic circuit may control the movable member.

In accordance with still further related embodiments of the invention, the assembly includes a control element for operating a pump cassette. The control element may include a bezel and a bezel gasket that includes a membrane capable of being displaced so as to operate the pump cassette. A pneumatic control circuit may be utilized to displace the membrane. A cassette receptacle may be movably coupled to one of the door and the assembly, the cassette receptacle capable of receiving the pump cassette. The movable member may be capable of pressing the cassette against the control element.

In accordance with another aspect of the invention, a door locking system includes an assembly having a first engagement means. A door attached to the assembly includes a second engagement means for engaging the first engagement means. The system further includes movable means for generating a force against at least one of the assembly and the door to press together and substantially prevent disengagement of the first engagement means and the second engagement means.

In accordance with another aspect of the invention, a method for locking a door is presented. The method includes providing an assembly that includes a first engagement surface. The assembly is coupled to a door, the door including a latch member having a second engagement surface for engaging said first engagement surface. The method further includes moving a movable member against at least one of the door and the assembly to press together and substantially prevent disengagement of the first engagement surface and the second engagement surface.

In accordance with related embodiments of the invention, the first engagement surface forms an undercut. The second engagement surface may have a projection for engaging the undercut.

In accordance with further related embodiments of the invention, a handle may be controlled to operate the latch member. Prior to moving the movable member against the one of the door and the assembly, the door may be closed and the handle moved such that the second engagement surface of the latch member is aligned to engage the first engaging surface. Opening the door may include moving the movable member away from the one of the door and the assembly. The handle can then be moved such that the second engagement surface is in non-alignment to engage the first engaging surface, allowing the door to be opened.

In accordance with still further related embodiments of the invention, moving the movable member against one of the assembly and the door includes expanding an expandable member, such as a bladder. The bladder may be pneumatically operated. A cassette receptacle may be attached to one of the door and the assembly. A pump cassette may be inserted into the cassette receptacle. The assembly may include a membrane capable of being displaced. The membrane may be pneumatically displaced to operate the pump cassette. The movable member may be moved against one of the pump cassette and the cassette receptacle to press the pump cassette against the membrane.

In accordance with other related embodiments of the invention, moving the movable member may include placing the movable member in contact with the at least one of the assembly and the door. An element may be placed between the at least one of the assembly and the door, such that the movable member contacts the element, such as a pump cassette, generating the force on the at least one of the assembly and the door.

BRIEF DESCRIPTION OF THE DRAWINGS

The foregoing features of the invention will be more readily understood by reference to the following detailed description, taken with reference to the accompanying drawings, in which:

FIG. 5A shows an exemplary blood processing system having a plurality of blood pumps in accordance with an embodiment of the present invention;

DETAILED DESCRIPTION OF ILLUSTRATIVE EMBODIMENTS

In illustrative embodiments of the present invention, a door locking system prevents accidental or otherwise inappropriate opening of a door. To that end, the locking system includes a latch member that is engaged by a latching structure and a movable member, which preferably is pneumatically controlled. When properly positioned, the movable member produces a force that essentially locks the latch member against the latching structure. An undercut feature on the latch member and/or the latching structure prevents disengagement of the latch member when the movable member is positioned. Details of various embodiments are discussed below.

Figure 1:
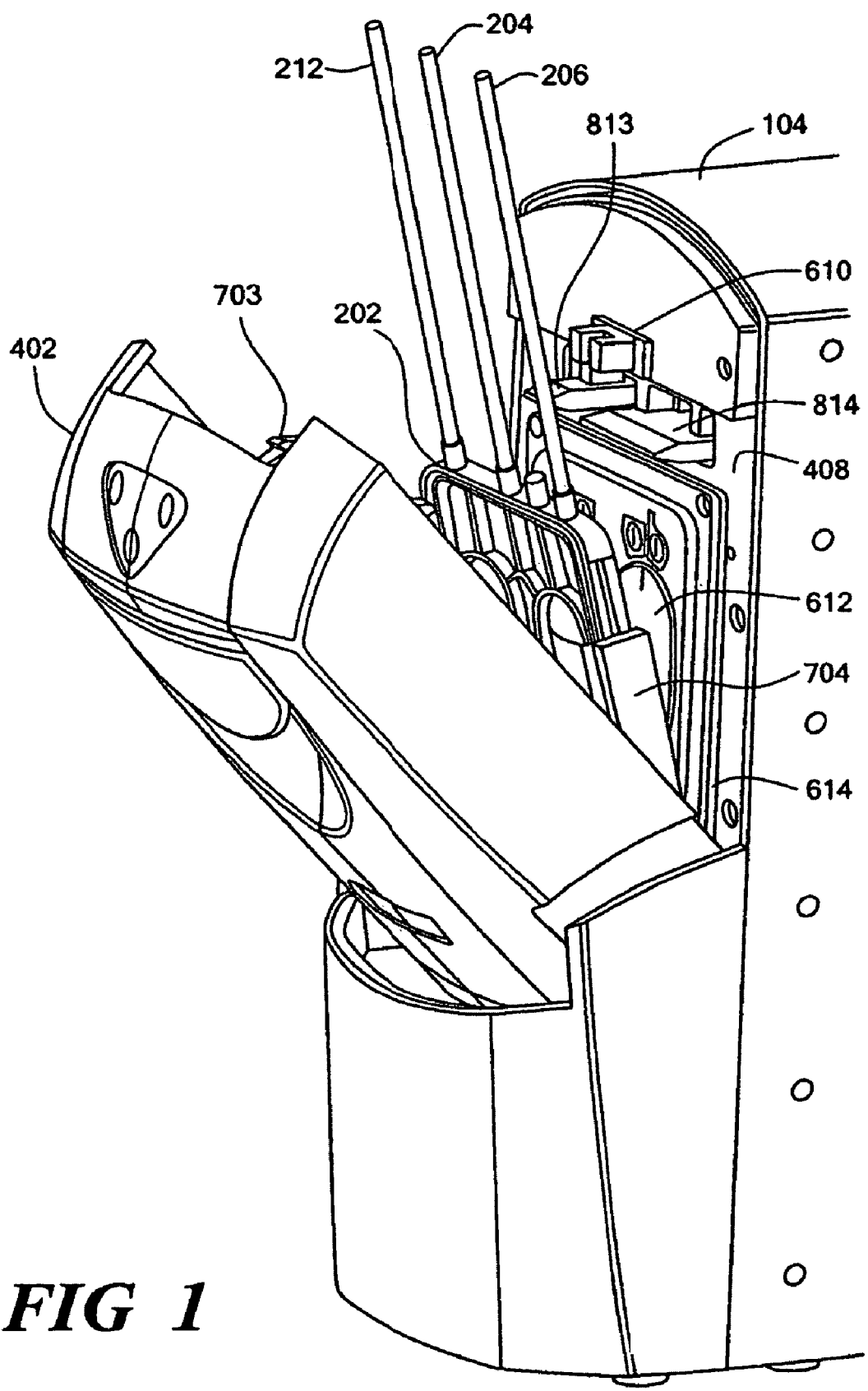
FIG. 1 is a schematic diagram showing a pump system that includes a door and assembly, in accordance with one embodiment of the invention.

FIG. 1 is a schematic diagram showing an assembly 104 that mixes liquids, such as blood and an anti-pathogen solution (discussed below). The assembly 104 includes, among other things, a front plate assembly 408 and a door 402 that is movably attached to the front plate assembly 408. The door 402 includes a latch member 703 for fastening closed the door 402 to the front plate assembly 408.

Figure 2:
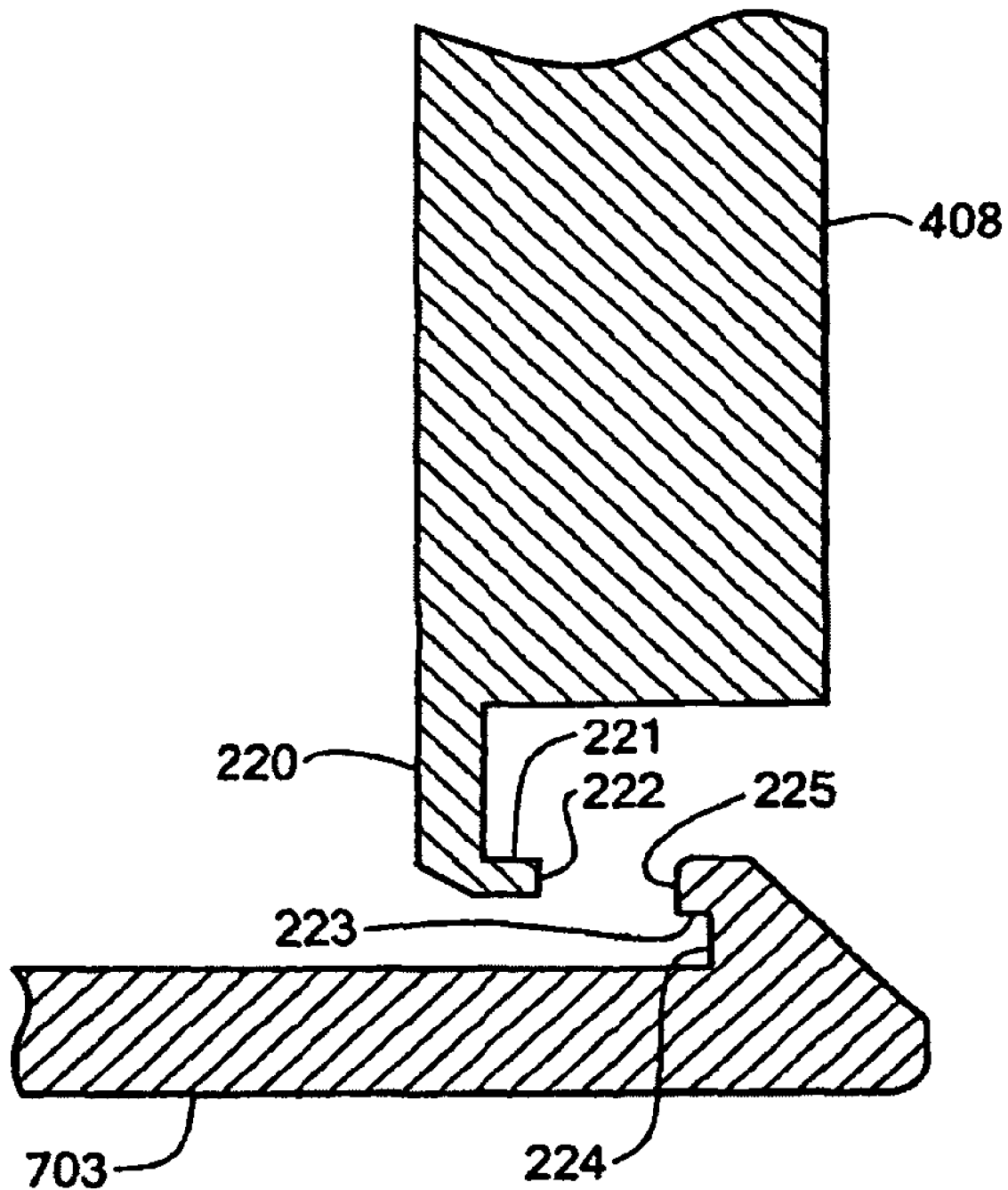
FIG. 2 shows a first engagement surface having an undercut, in accordance with one embodiment of the invention.

As shown in FIG. 2, the front plate assembly 408 includes a latching structure 220 for engaging the latch member 703. The latching structure 220 has an undercut feature forming surfaces 221 and 222. Similarly, the latch member 703 has an undercut feature forming surfaces 223 and 224. In order to close the door, the door must be rotated inward past its locking position such that surface 225 travels beyond surface 222, at which point the latch member 703 can be rotated upward such that the surface 223 travels above surface 221. When the door 402 is closed, the latch member 703 is engaged by the latching structure 220 such that the surface 223 overlaps the surface 221. Opposing forces are placed on the latch member 703 and the front plate assembly 408 such that the surfaces 222 and 224 are forced toward one another. With the latch member 703 so engaged, the surface 221 prevents the latch member 703 from being rotated or otherwise displaced downward due to contact with the surface 223 and therefore prevents disengagement of the latch member 703 from the latching structure 220. When the opposing forces are removed or overcome, the door 402 and latch member 703 can be pushed inward toward the front plate assembly 408 until the surface 223 no longer overlaps the surface 221 and the latch member 703 can be rotated or otherwise displaced downward to as to disengage the latch member 703 from the latching structure 220.

Figure 3A:
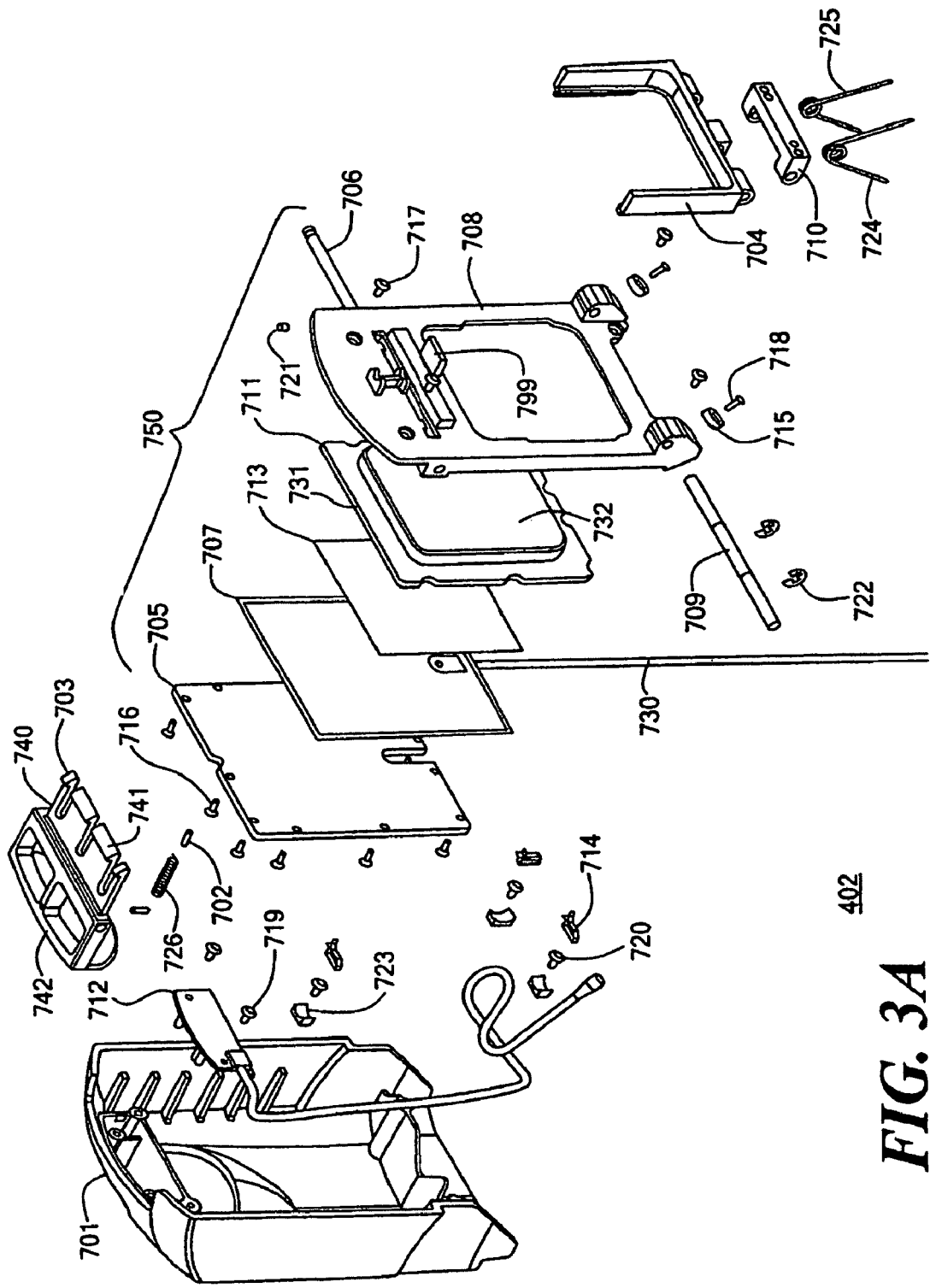
FIG. 3A shows an exploded view of the door assembly in accordance with an embodiment of the present invention.

FIG. 3A shows an exploded view of an exemplary embodiment of the door 402. Among other things, the door assembly 402 includes a door cowl 701, a latch spring post 702, a door latch 703, a cassette receptacle 704, a back plate 705, a latch pin 706, a bladder 707 with an attached pneumatic circuit 730, a frame 708, a door pin 709, a door mounting bracket 710, a piston assembly 711 including a piston plate 731 and a piston cover 732, a human interface board assembly 712, double coated tape 713, a miniature cable tie 714, recessed bumpers 715, E-rings 722, cable tie mount 723, torsion springs 724 and 725, extension spring 726, a cassette orientation tab 799, and various screws 716, 717, 718, 719, 720, and 721. The human interface board assembly 712 is mounted to the inside of the door cowl 701. The door 402 movably attaches to the assembly 104 via a door mounting bracket 710. The door 402 includes the latch member 703, which includes a post 740 that extends through the door 701. The post 740 includes a projection 741, for engaging the first engagement surface 220 of the assembly 104, as described above. The cassette receptacle 704 is pivotally mounted to the frame 708 using the door mounting bracket 710, the door pin 709, and the E-rings 722. Recessed bumpers 715 reduce strain on the door if the door is opened too far or with excessive force. The torsion springs 724 and 725 aid the operator in closing the door, as the door has considerable weight due to the many components. The cassette orientation tab 799 prevents the door from being closed if the pump cassette is oriented incorrectly in the cassette receptacle 704.

The latch member 703 may include a handle 742 attached to the post 740, which is accessible from a front side of a door cowl 701. Manipulation of the handle 742, such as by pulling up on the handle 742, changes alignment of the projection 741 relative to the first engagement surface 220 of the assembly 104. When the projection 741 is aligned with the first engagement surface 220, the door 402 is prevented from being opened due to engagement of the projection 741 with the first engagement surface 220. Alternatively, when the projection 741 is not aligned with the first engagement surface 220, the door 402 is free to swing open.

Latch member 703 may be spring-loaded and thus, include a spring 726 guided by a latch spring post 702. The spring 726 places a force on the latch member 703 so that when the door 402 is closed, the projection 741 on latch member 703 snaps into alignment with the first engagement surface 220 of the assembly 104. To ensure that the door 402 is properly closed, initial alignment of the latch member 703 with the first engagement surface 220 may produce a distinct sound, or cause tactile feedback on the handle 742 that can be felt by the operator.

To open the door 402, the operator pushes the door 402 inward toward the front plate assembly 408 until the surface 223 no longer overlaps the surface 221 and rotates the handle 742 upward, overcoming the force placed on the latch member 703 by the spring 726 and rotating the latch member 703 downward so as to clear the latching structure 220. The door 402 can then be pulled open.

In accordance with illustrative embodiments of the invention, a movable member prevents accidental and/or inappropriate opening of the closed and latched door 402. To that end, the movable member is capable of generating a force against at least one of the front plate assembly 408 and the door 402 to press together and substantially prevent backing out and disengagement of the latch member 703.

The movable member may be a piston assembly, such as the piston assembly 711, operated by an expandable member, such as the bladder 707. The expandable member may be made from, among other things, elastic, resilient, and/or flexible material(s). In other exemplary embodiments, the movable member may be a rigid structure controlled by, for example, a motor.

The bladder 707 may be coupled to the piston assembly 711, which provides a surface for making contact with the assembly 104. Among other things, using the piston assembly 711 advantageously reduces wear on the bladder 707. The piston assembly 711 may attach to the bladder 707 using, for example, various adhesives known in the art, such as glue and/or tape 713, which may be double-sided tape. The piston assembly 711 may include a rigid plate 731 made of, for example, a hard plastic, that includes a protrusion that is covered by a piston cover 732. The piston cover 732 can be made of an elastomer. When the bladder 707 inflates, the piston assembly 711 is pushed toward the frame 708 such that the piston cover 732 protrudes through the frame 708 so that it can be pressed, and in various embodiments, sealed against a surface on the front plate assembly 408 or another element (such as a pump cartridge placed in a cassette receptacle 704, described in detail below) positioned between the frame 708 and the front plate assembly 408.

For support, the piston assembly 711 and bladder 707 are sandwiched between a rigid back plate 705 and the frame 708, which are mechanically coupled together to form a frame assembly 750. The frame assembly 750 is mounted to the inside of the door cowl 701 so that the door latch 703 protrudes through the frame assembly 750 and the frame assembly 750 holds the door latch 703 in place via latch pin 706. In other embodiments of the present invention, the frame assembly 750 can be mounted to the assembly 104.

The bladder 707 is coupled to, and controlled by, a pneumatic circuit 730 that provides positive and/or negative air pressure to the bladder 707. Positive pressure supplied to the bladder 707 causes the bladder 707 to expand in the direction of the frame 708, since the back plate 707 prevents the bladder from expanding in the direction of the door cowl 701. This, in turn, causes the piston assembly 711 to move toward the front plate assembly 408, such that the piston cover 732 presses against the front plate assembly 408 or other element positioned between the piston cover 732 and the front plate assembly 408 (such as a pump cassette positioned within the cassette receptacle 704), thereby producing an outward force on the door 402 away from the front plate assembly 408. Alternatively, supplying negative pressure to the bladder 707 causes the piston assembly 711 to move away from the front plate assembly 408 (or other element), thereby reducing the outward force on the door 402 away from the front plate assembly 408.

With a pump cassette positioned in the cassette receptacle 704 and the door 402 in a closed position, pneumatically inflating the bladder 707 to move the piston assembly 711 toward the front plate assembly 408 causes the pump cassette to be pressed firmly against a bezel assembly on the front plate assembly 408, which in turn produces an outward force on the door 402 away from the front plate assembly 408. This outward force on the door 402 firmly engages the latch member 703 and the latching structure 220, specifically by forcing the surfaces 222 and 224 toward one another (see FIG. 2). With the latch member 703 so engaged, the surface 221 prevents the latch member 703 from being rotated or otherwise displaced downward due to contact with the surface 223 and therefore prevents disengagement of the latch member 703 from the latching structure 220. As a result, the door 402 is locked, and the door 402 generally cannot be opened until the bladder is pneumatically deflated.

The pneumatic circuit 730 may be precisely controlled by a control unit 751 that inflates the bladder 707 based on characteristics of the particular door 402 and/or front plate assembly 408. The control unit 751 may include, in part, a microprocessor with associated sensors, logic, and/or memory as known in the art. The control unit 751 may control the movable member based on any number of various interlocks. Accidental or inadvertent manipulation of the handle will not open and/or close the door unless these various interlocks are met.

Figure 3B:
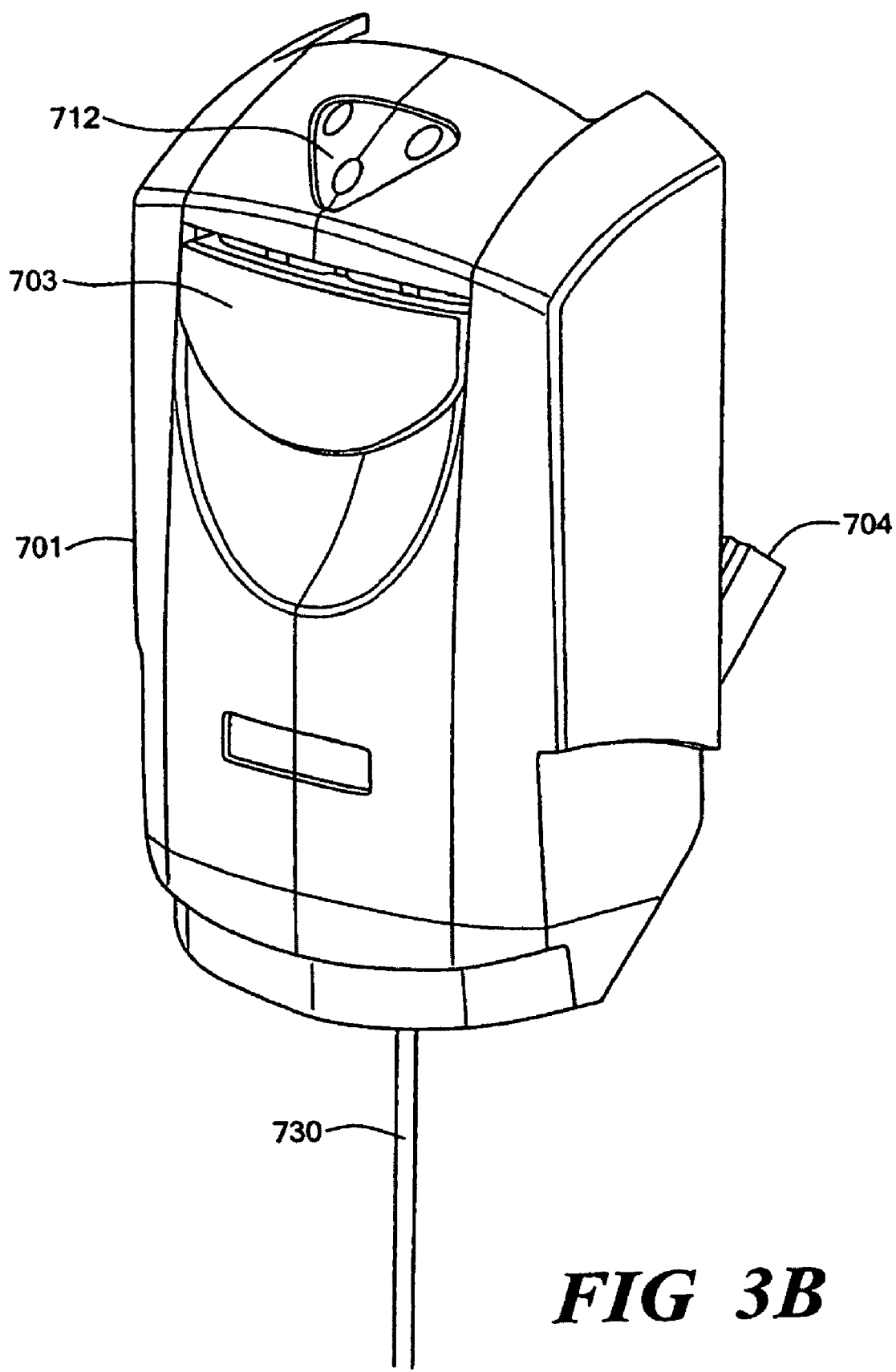
FIG. 3B shows a front perspective view of the door assembly in accordance with an embodiment of the present invention.

FIG. 3B shows a front perspective view of the door assembly 402 shown in FIG. 3A. A human interface board assembly 712 having LEDs or other operator controls, and the handle portion of the door latch 703, are visible from the front of the door cowl 701. A portion of the cassette receptacle 704 and the pneumatic circuit 730 are also visible.

Figure 3C:
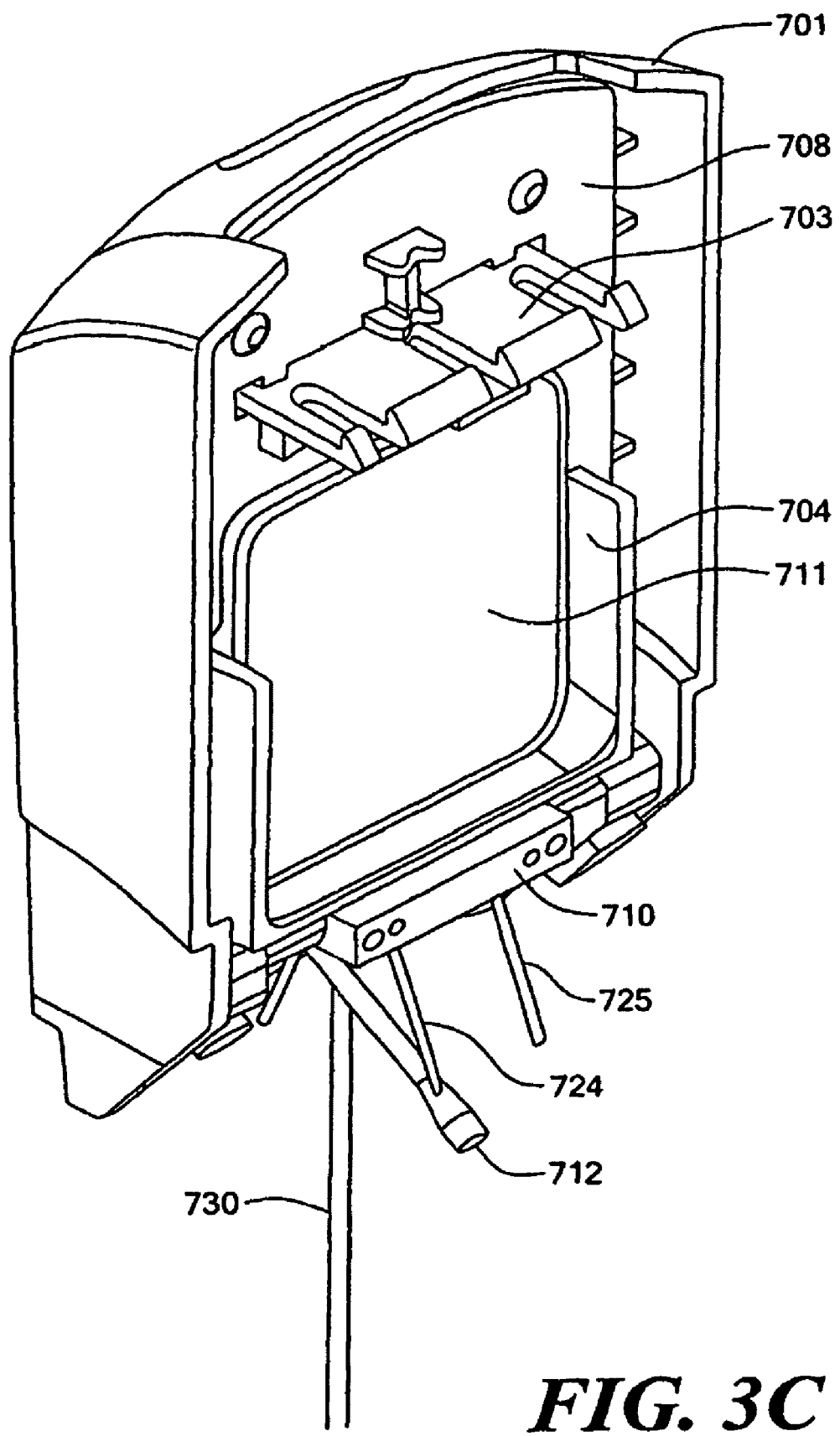
FIG. 3C shows a rear perspective view of the door assembly in accordance with an embodiment of the present invention, in which the cassette receptacle is in a retracted position.

FIG. 3C shows a rear perspective view of the door assembly 402 shown in FIG. 3A, in which the cassette receptacle 704 is in a retracted position. Visible at the rear of the door cowl 701 are the frame 708, the latch portion of the door latch 703, the cassette receptacle 704, the piston assembly 711, the door mounting bracket 710, torsion springs 724 and 725 (which can aid the operator in closing the door, as the door has considerable weight due to the many components), a portion of the human interface board assembly 712, and a portion of the pneumatic circuit 730.

Figure 3D:
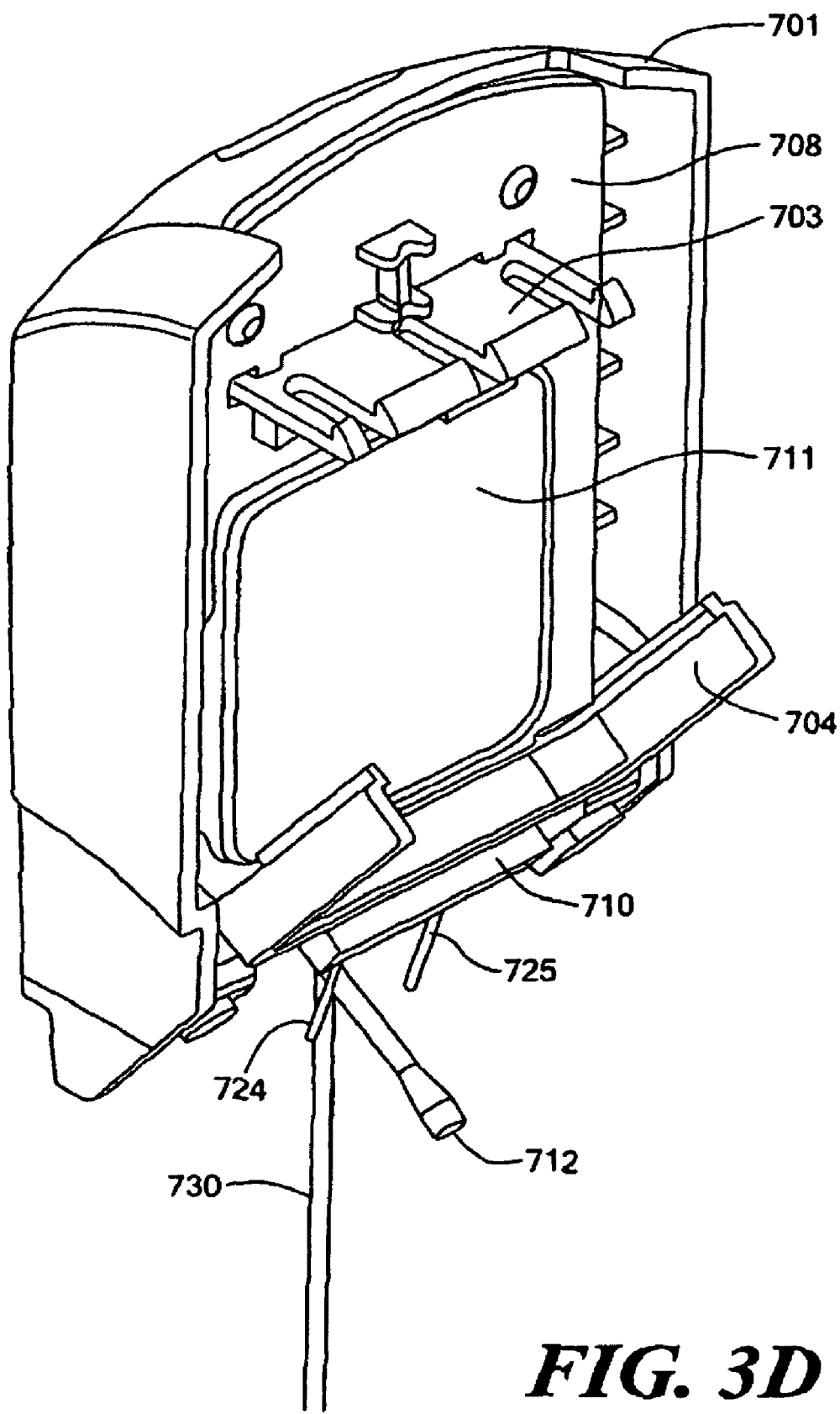
FIG. 3D shows a rear perspective view of the door assembly in accordance with an embodiment of the present invention, in which the cassette receptacle is in an open position.

FIG. 3D shows a rear perspective view of the door assembly 402 shown in FIG. 3A, in which the cassette receptacle 704 is in an open position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

As discussed above, the door must typically be rotated inward past its locking position in order to close and open the door. In order to lock the door when the door is closed, a force is applied by a movable member such that the latch member is locked against the latching structure. Among other things, the movable member prevents or otherwise restricts inward rotation of the door, making it difficult or impossible to open the door when it is locked.

As discussed below, the assembly 104 typically includes an occluder assembly for occluding one or more pliable plastic tubes coupled to the pump cassette. The occluder assembly is typically attached to the back of the front plate assembly 408, and includes one or more occluder blades that protrude through openings in the front plate assembly 408 and make contact with corresponding structures on the door assembly 402 when the door 402 is in a closed position. Each occluder blade is typically spring loaded and is pneumatically controlled to permit extension and retraction of the occluder blade. In exemplary embodiments of the invention, each occluder blade is held in an extended position by a flat spring and is retracted by inflating a bladder positioned under the spring so as to deflect, and thereby shorten the effective length of, the spring.

In typical embodiments of the invention, the occluder blades are positioned so that, when they are in an extended position, they make contact with the door 402 before the latch member 703 is engaged by the latching structure 220. In order to close or open the door, the door 402 must be rotated inward toward the front plate assembly 408 beyond the extended position of the occluder blades. The occluder blades can be retracted to facilitate closing and opening of the door. If, however, the occluder blades are not retracted (for example, due to a loss of power), then the door 402 must be rotated inward toward the front plate assembly 408 with a force sufficient to overcome the occluder springs and deflect the occluder blades inward in order to close or open the door.

Figure 3E:
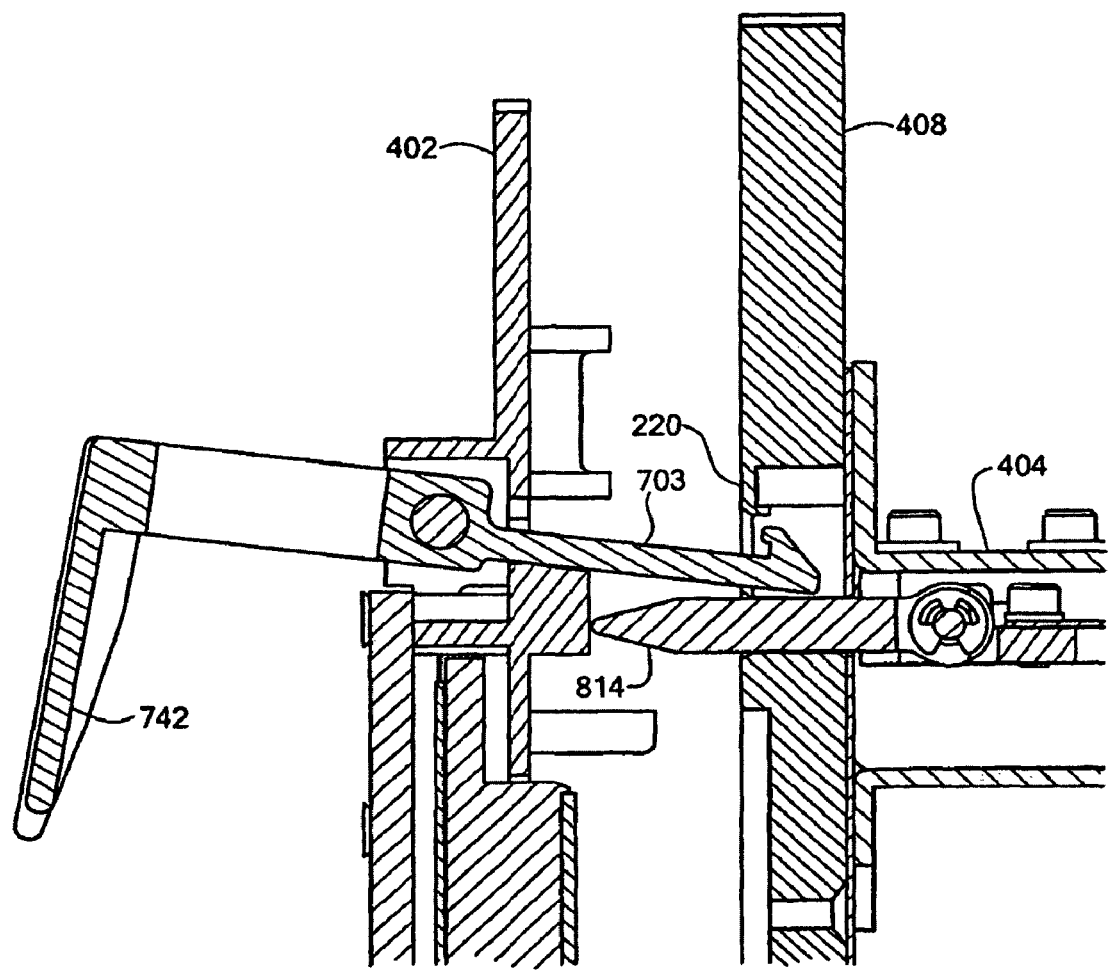
FIG. 3E shows a cross-sectional view of an exemplary door lock system with the door in contact with an occluder blade and the latch member in an unlatched position, in accordance with an embodiment of the present invention.

FIG. 3E shows a cross-sectional view of an exemplary door lock system with the door 402 in contact with an occluder blade 814 and the latch member 703 in an unlatched position, in accordance with an embodiment of the present invention. The occluder blade 814 is a component of an occluder assembly 404 that is attached to a back side of the front plate assembly 408, with the occluder blade 814 protruding through a slot in the front plate assembly 408. The occluder blade 814, which is spring loaded, prevents the door 402 from closing and latching unless and until the door 402 is rotated inward with sufficient force to overcome the occluder spring.

Figure 3F:
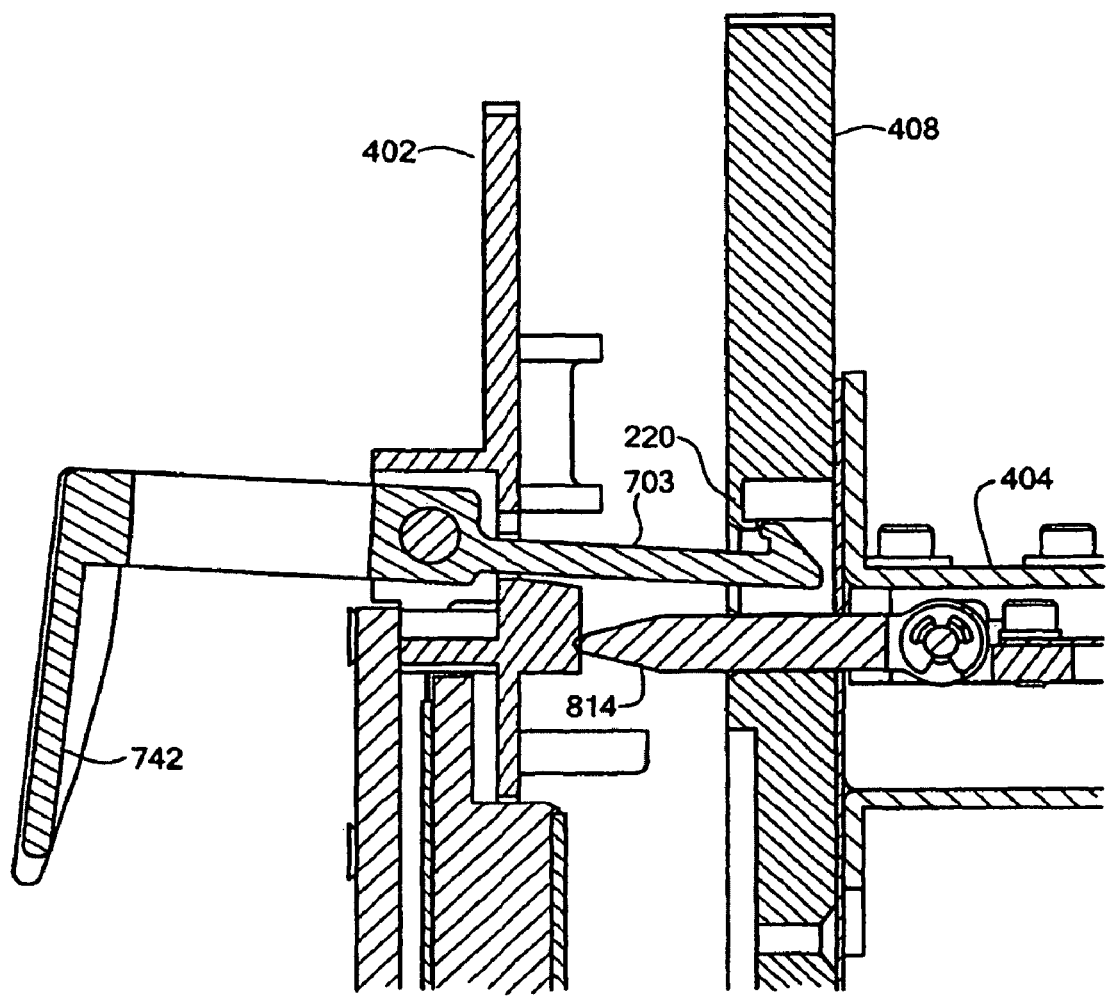
FIG. 3F shows a cross-sectional view of an exemplary door lock system with the door rotated inward sufficiently to overcome the occluder springs and the latch member in an unlatched position, in accordance with an embodiment of the present invention.

FIG. 3F shows a cross-sectional view of an exemplary door lock system with the door 402 rotated inward sufficiently to overcome the occluder springs and the latch member 703 in an unlatched position, in accordance with an embodiment of the present invention. The occluder blade 814 is shown in its fully extended position so as to demonstrate the amount of door rotation needed to overcome the occluder springs.

Figure 3G:
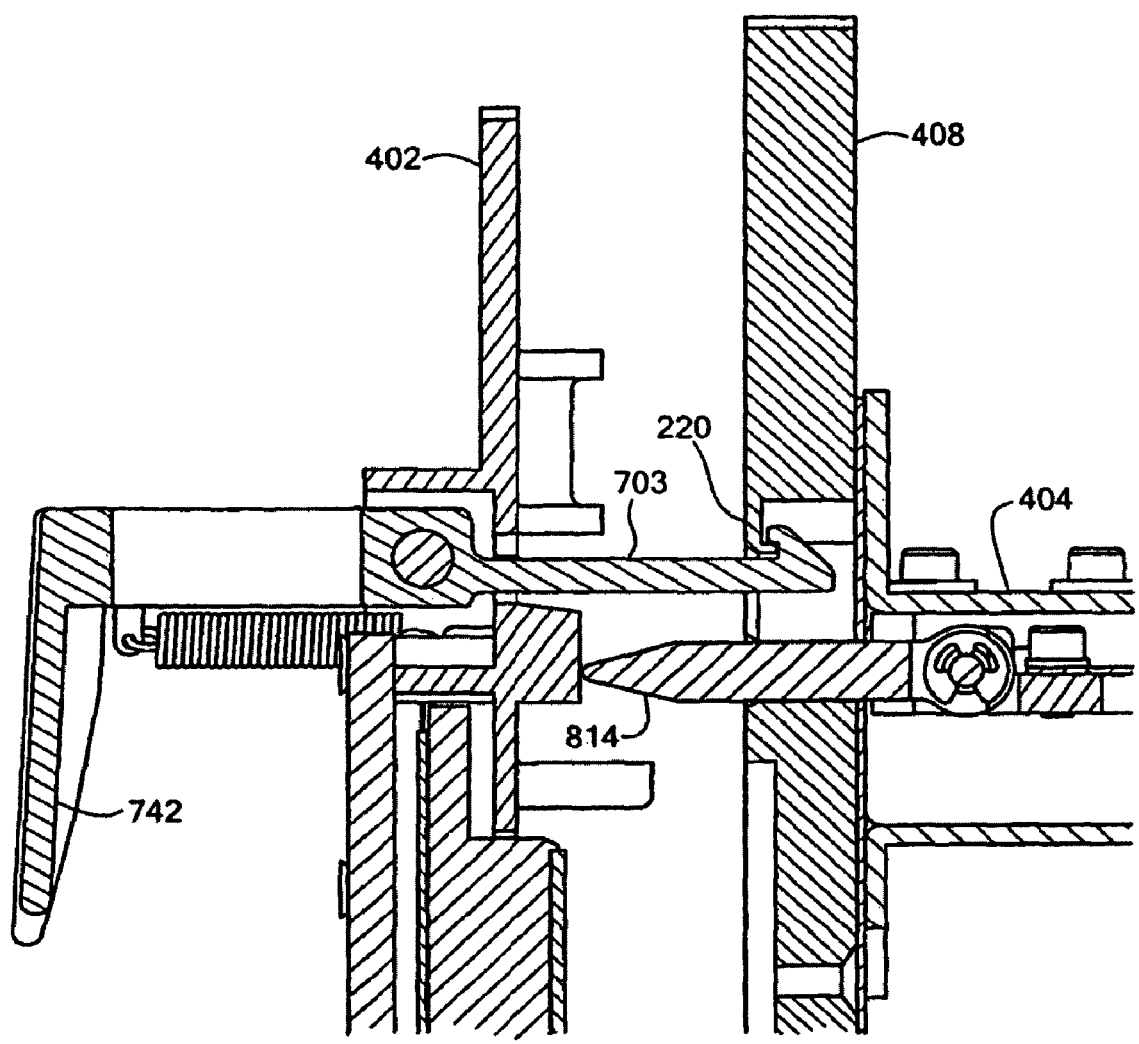
FIG. 3G shows a cross-sectional view of an exemplary door lock system with the door fully closed and the latch member in a latched position, in accordance with an embodiment of the present invention.

FIG. 3G shows a cross-sectional view of an exemplary door lock system with the door fully closed and the latch member in a latched position, in accordance with an embodiment of the present invention. In this position, the latch member 703 is fully engaged by the latching structure 220 of the front plate assembly 408, and the occluder blade 814 is deflected inward. In order to open the door 402 from this position, the door 402 must be rotated inward until the surface 223 no longer overlaps the surface 221, at which time the handle 742 can be lifted, causing the latch member 703 to rotate downward clear of the latching structure 220.

Figure 4:
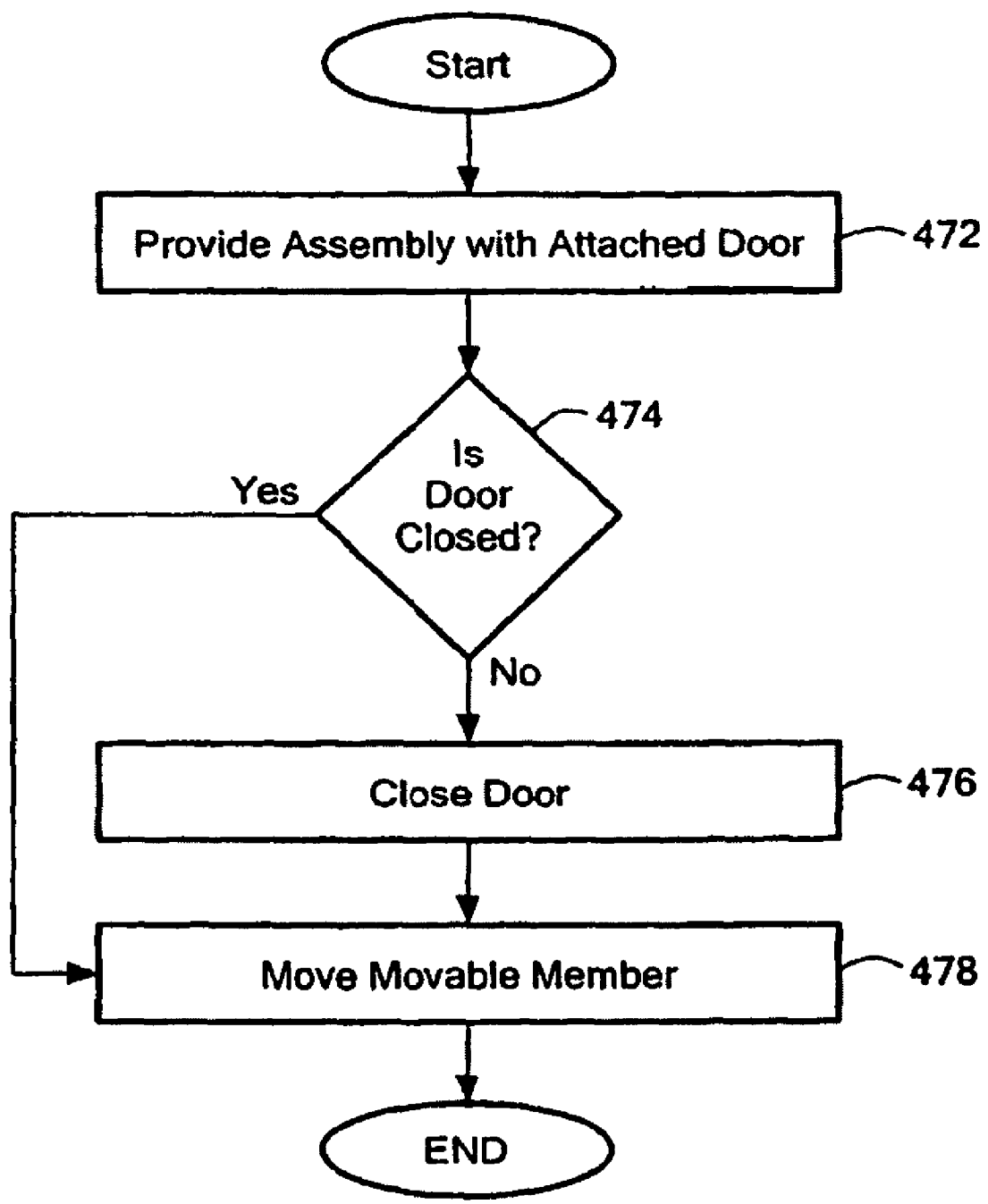
FIG. 4 is a process flow diagram describing a process for locking a door, in accordance with one embodiment of the invention.

FIG. 4A shows a process for locking the door 402, in accordance with an embodiment of the present invention. In block 472, the assembly 104 including the front plate assembly 408 and the attached door assembly 402 is provided. As shown in FIG. 2, the front plate assembly 408 includes a latching structure 220 having an undercut feature defining surfaces 221 and 222, and the door assembly 402 includes a latch member 703 including an undercut feature defining surfaces 223 and 224. The process continues by checking if the door 402 is open, in block 474.

If the door 402 is open, the door 402 is closed in block 476. As discussed above, the door 402 is preferably closed by rotating the door 402 inward toward the front plate assembly 408 with sufficient force to overcome the force of the occluders until the latching structure 220 engages the latch member 703 such that the surface 223 overlaps the surface 221. Closing the door 402 may be facilitated by rotating the latch member 703 downward (e.g., by pulling up on the handle 742) while rotating the door 402 inward. The latch member 703 is preferably spring loaded, allowing the latch member 703 to engage with the latching structure 220 when the door 402 is rotate inward sufficiently.

When the door 402 is closed (or if the door 402 was already closed), the process continues by moving a movable member against at least one of the door 402 and the front plate assembly 408, in block 478. In exemplary embodiments of the invention, the movable member includes an inflatable bladder that is situated in the door 402 and, when inflated (represented by arrow 797 in FIG. 3G), pushes against an installed pump cassette and the front plate assembly 408 so as to produce a net outward force on the door 402 away from the front plate assembly 408 (represented by allow 798 in FIG. 3G). The movable member causes the surfaces 222 and 224 to be forced toward one another. With the latch member 703 so engaged, the surface 221 prevents the latch member 703 from being rotated or otherwise displaced downward due to contact with the surface 223 and therefore prevents disengagement of the latch member 703 from the latching structure 220. Opening of the door 402 by accidental or inappropriate manipulation of the handle 742 is thus prevented. The system described above may be used in a wide variety of applications. In exemplary embodiments of the present invention, an anti-pathogen solution can be mixed with a red blood cell concentrate (RBCC) to form an incubation solution for reducing pathogens in the RBCC. The anti-pathogen solution is prepared by mixing a caustic anti-pathogen compound (e.g., PEN110™ or INACTINE™, which is an organic solvent with a pH over 11 that is distributed by V.I. Technologies, Inc. of Watertown, Mass.) with a buffer solution of sodium phosphate to a predetermined concentration (e.g., 1 part anti-pathogen compound to 99 parts buffer solution), preferably as described in Application D70. For convenience, this mixing of anti-pathogen compound with buffer solution may be referred to hereinafter as "compounding," and an apparatus that performs such compounding may be referred to hereinafter as a "compounder" or "compounder pump." The incubation solution is prepared by mixing the anti-pathogen solution with the RBCC to a predetermined concentration (e.g., 1 part anti-pathogen solution to 9 parts RBCC), as described below. For convenience, this mixing of anti-pathogen solution with RBCC may be referred to hereinafter as "blood processing," and an apparatus that performs such blood processing may be referred to hereinafter as a "blood pump." Due to the caustic nature of the anti-pathogen compound, the system remains must remain in a closed environment to prevent the operator from being harmed during compounding/blood processing. Details of a blood processing system incorporating the illustrative door locking system follow below.

System Overview

FIG. 5A shows an exemplary blood processing system 100 having a plurality of blood pumps in accordance with an embodiment of the present invention. Among other things, the blood processing system 100 includes a single compounder pump 102 and ten essentially identical blood pumps 104 organized as two banks of five blood pumps each. The compounder pump 102 pumps buffer solution from a buffer solution container 110 into a vial of anti-pathogen compound 108. The mixture, referred to as a working solution, is pumped into a working solution container 112. Each of the blood pumps 104 mixes working solution from the working solution container 112 with red blood cell concentrate (RBCC) from a RBCC container 106 to form an incubation solution that is pumped into an incubation bag 118. The incubation solution is typically allowed to incubate for some period of time, after which it is rinsed to remove the anti-pathogen compound to produce a pathogen reduced blood product. The blood processing system 100 typically also includes two sterile docks 114 that are used by the operator to splice together plastic tubing as necessary for various blood processing operations. The blood processing system 100 is controlled through a user interface 116.

Figure 5B:
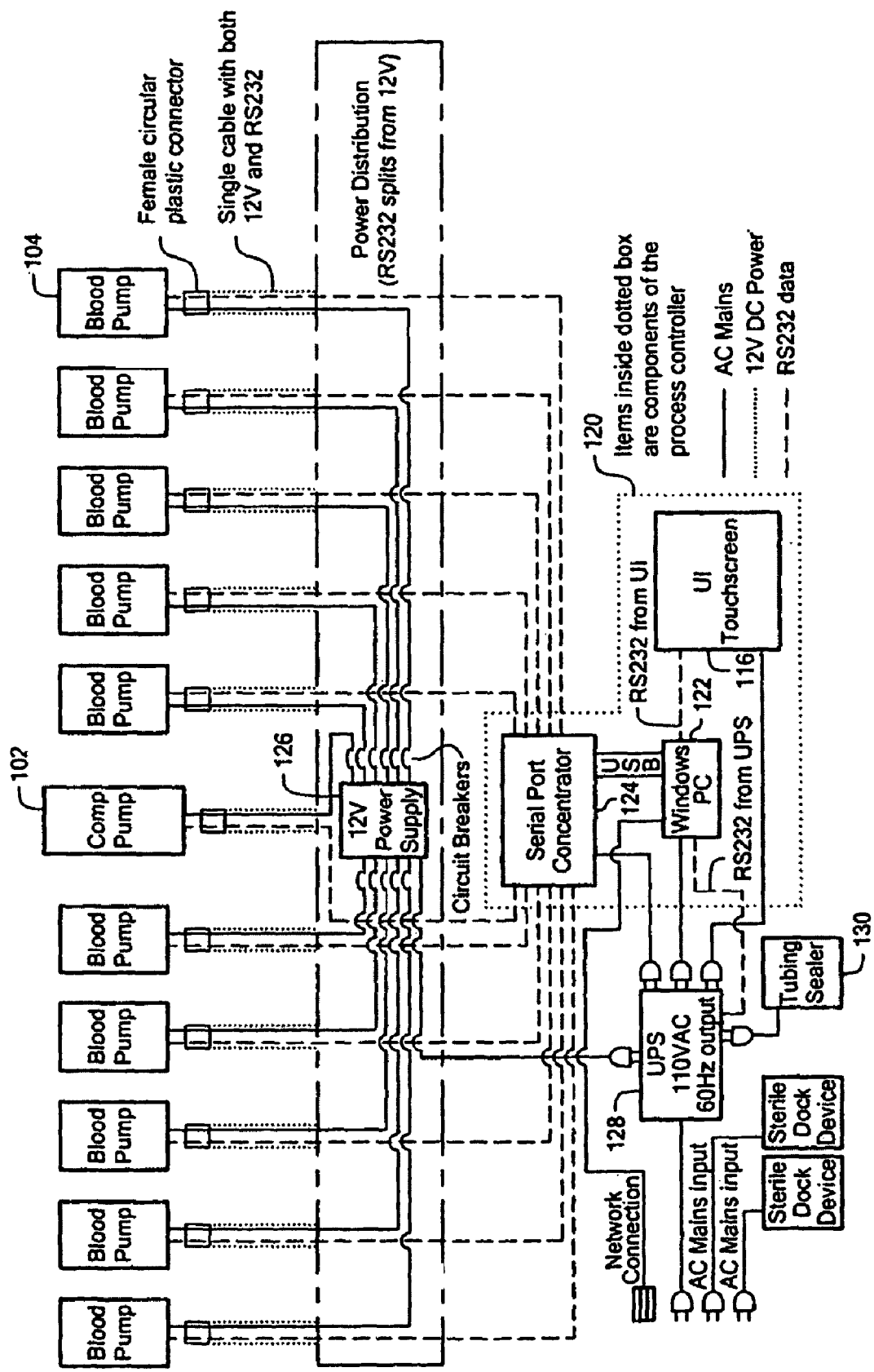
FIG. 5B shows an exemplary wiring diagram for one embodiment of the blood processing system shown in FIG. 1A.

FIG. 5B shows an exemplary wiring diagram for one embodiment of the blood processing system 100. The compounder pump 102 and the blood pumps 104 are typically powered from a common. 12-Volt external power supply 126, and are controlled by an external process controller 120. The process controller 120 includes the user interface 116, a computer 122, and a serial port concentrator 124. The compounder pump 102 and the blood pumps 104 are in communication with the process controller 120 through the serial port concentrator 124, for example, over RS-232 communication links. The blood processing system 100 typically includes a tubing sealer 130 for sealing plastic tubing as necessary for various blood processing operations. The blood processing system 100 typically includes an uninterruptible power supply (UPS) 128 for maintaining electrical power to the 12-Volt power supply, the process controller, and other components in the event of a primary power loss.

Figure 5C:
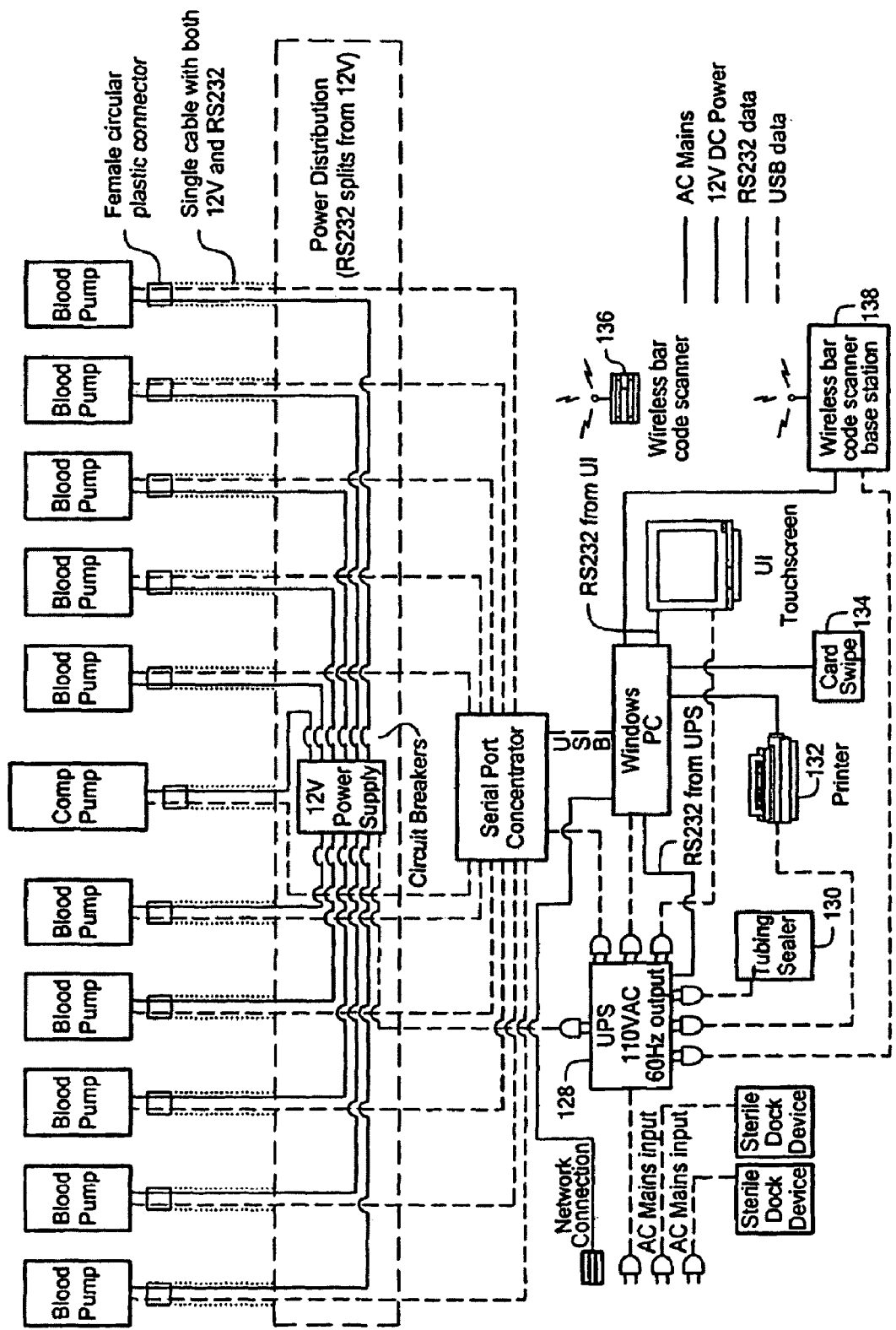
FIG. 5C shows an exemplary wiring diagram for another embodiment of the blood processing system shown in FIG. 1A.

FIG. 5C shows an exemplary wiring diagram for another embodiment of the blood processing system 100. The blood processing system 100 may include a printer in communication with the process controller for printing out reports. The blood processing system 100 may include a card reader 134 in communication with the process controller for card-based operator identification. The blood processing system 100 may include a wireless bar code scanner base station 138 in communication with the process controller for receiving bar code information scanned using a wireless bar code scanner 136. Bar codes are typically used to track the various solution containers and the pumps on which those containers were processed.

The process controller 120 coordinates the actions of the compounder pump 102, the blood pumps 104, and the operator throughout the various mixing operations, as described in greater detail in Application D72. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations.

When the blood processing system 100 is operating from the uninterruptible power supply 128 and at other appropriate times, the process controller 120 will prevent compounding and other pump operations from starting, although the pumps will generally be allowed to complete any ongoing operations. Furthermore, if the process controller fails, the pumps have internal logic for safely completing or terminating any ongoing operations.

Blood Disposables

In an exemplary embodiment of the present invention, the process controller 120 coordinates blood processing for an entire bank of five blood pumps 104 at a time. Specifically, five pump cassettes, each connected to a RBCC container and an incubation bag for receiving the incubation solution, are loaded respectively into the five blood pumps 104. The five pump cassettes are preferably connected by a single working solution inlet tube to the working solution container so that all five blood pumps draw working solution from the single working solution container. For convenience, the five interconnected pump cassettes along with their respective incubation bags and various plastic tubing may be referred to hereinafter as a "blood disposables set." The blood disposables set is preferably used for a single blood processing cycle and is then discarded. The blood disposables set is described in greater detail in Application D85.

Figure 6:
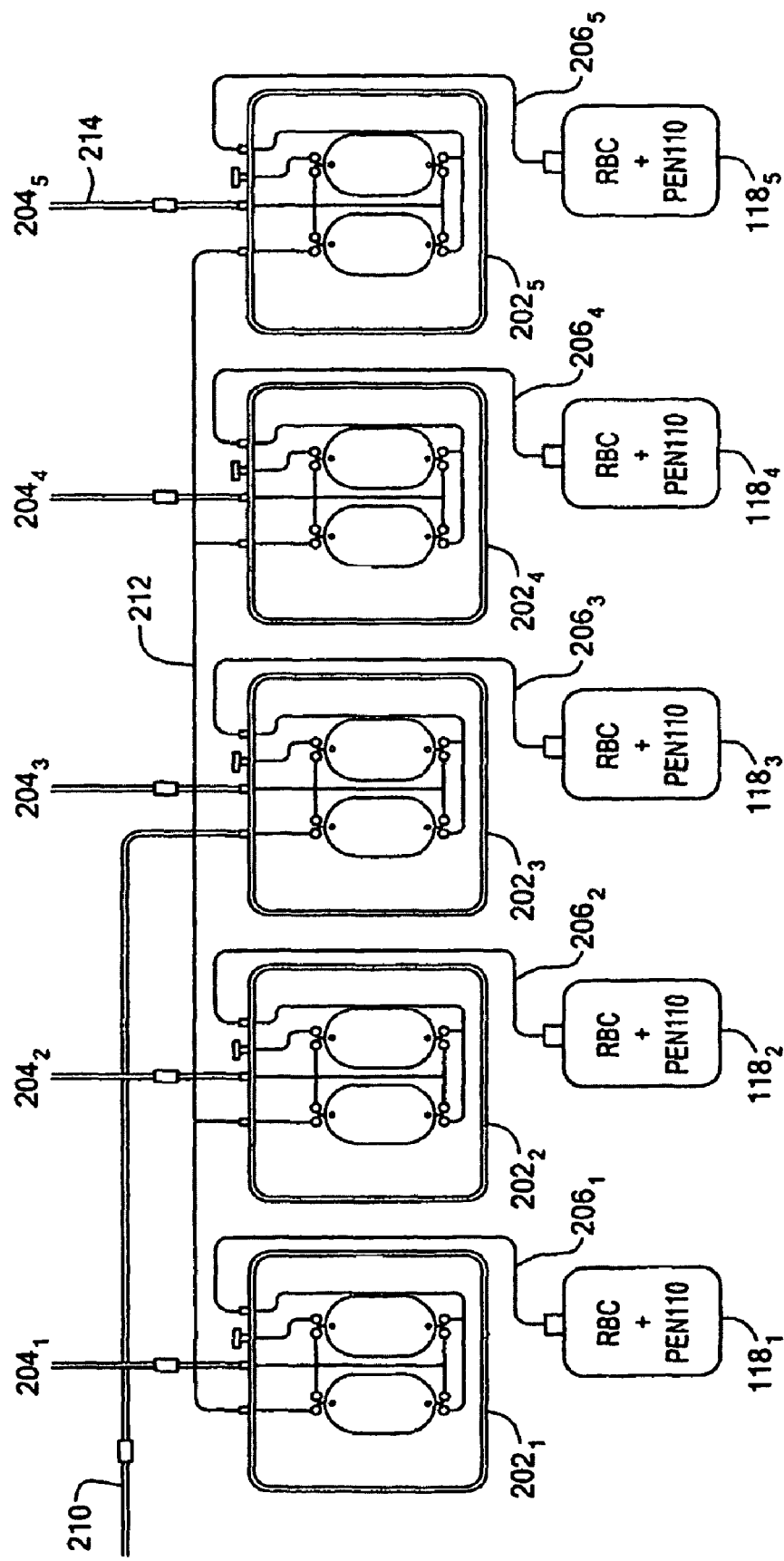
FIG. 6 shows an exemplary blood disposables set in accordance with an embodiment of the present invention.

FIG. 6 shows an exemplary blood disposables set 200 in accordance with an embodiment of the present invention. The blood disposables set 200 includes five pump cassettes 202.sub.1-5, each respectively having a RBCC inlet tube 204.sub.1-5 connected to an RBC inlet port of the pump cassette and an incubation solution outlet tube 206.sub.1-5 connected to an outlet port of the pump cassette and to an incubation bag 118.sub.1-5. The blood disposables set 200 also includes working solution distribution tubing 212 that connects to a working solution inlet port on each pump cassette 202.sub.1-5 and to a single working solution inlet tube 210 so that the working solution inlet ports of all pump cassettes 202.sub.1-5 are effectively connected to the single working solution inlet tube 210. The working solution inlet tube 210 preferably connects to the working solution distribution tubing 212 close to where the working solution inlet port of the middle pump cassette 202.sub.3 connects to the tubing 212, and the working solution inlet ports of each concentric pair of pump cassettes is preferably connected to the tubing 212 a substantially equal distance from that center connection such that the working solution inlet ports of the pump cassettes 202.sub.1 and 202.sub.5 are essentially equidistant from the center connection and the working solution inlet ports of the pump cassettes 202.sub.2 and 202.sub.4 are essentially equidistant from the center connection. Among other things, this spacing of pump cassettes along the tubing 212 facilitates priming of the pumps, as discussed below. In order to perform blood processing, each RBCC inlet tube 204 is connected to a separate RBCC container 106, and the working solution inlet tube 210 is connected to the common working solution container 112. The blood disposables set 200 also includes six break-away closures 214, one on each of the RBCC inlet tubes 204 and one on the working solution inlet tube 210. In order to reduce the likelihood of confusing which RBCC bag and which incubation bag is associated with each pump cassette, the RBCC inlet tubes 204 and the incubation solution outlet tubes 206 are preferably coded, for example, by alternating between color-striped and clear tubing from cassette to cassette.

Figure 7A:
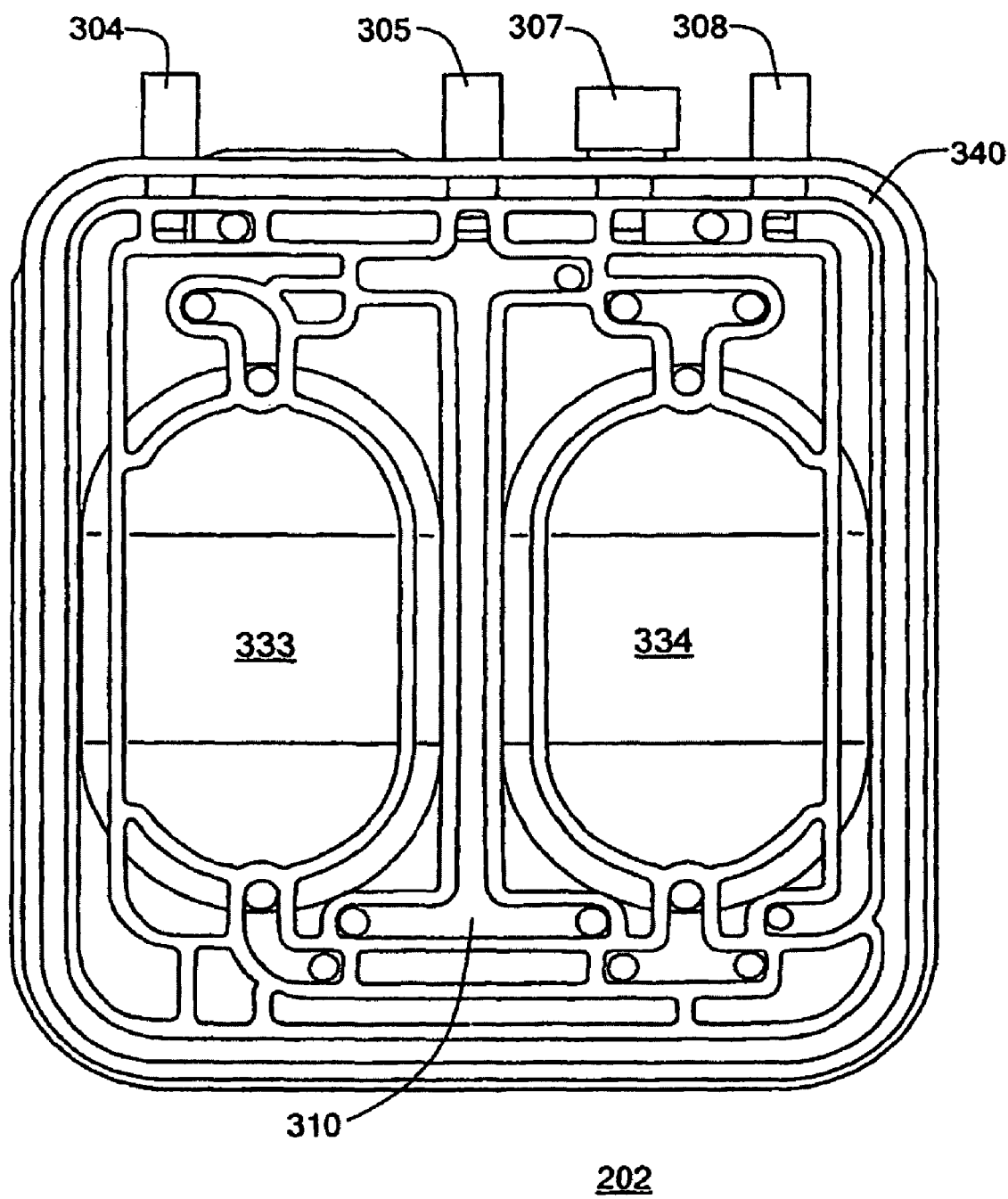
FIG. 7A shows a front view of the pump cassette in accordance with an embodiment of the present invention.

FIG. 7A shows a front view of the pump cassette 202 in accordance with an embodiment of the present invention. The pump cassette 202 is essentially a rigid core including formations and sealing ribs 340 constituting various pumping chambers, fluid valves, and fluid pathways (channels). The rigid core is covered on each side by a flexible membrane (e.g., a flexible PVC sheet). The flexible membranes seal against the core and isolate the blood pump 104 from fluids within the cassette. The pump cassette 202 is designed to interface with the blood pump 104 in only one direction. For example, the pump cassette 202 typically includes an asymmetric feature (such as the placement of tubing) that prevents the blood pump door from closing if the pump cassette 202 is inserted incorrectly.

Among other things, the pump cassette 202 includes a working solution inlet port 304, an RBC inlet port 305, a vent port 307, an outlet port 308 and two pumping chambers, namely a working solution chamber 333 and an RBC chamber 334. During blood processing, working solution from the working solution container 112 is drawn into the working solution chamber 333 through the tubing 210 and 212 and the working solution inlet port 304, and is pumped from the working solution chamber 333 into the channel 310 while RBCC from the RBCC container 106 is drawn into the RBC chamber 334 through the RBCC inlet tube 204, the RBCC inlet port 305, and the channel 310. This causes the working solution and RBCC to be mixed within the channel 310 and the RBC chamber 334. The mixture (incubation solution) is pumped from the RBC chamber 334 to the incubation bag 118 through the outlet port 308 and the incubation solution outlet tube 206.

Figure 7B:
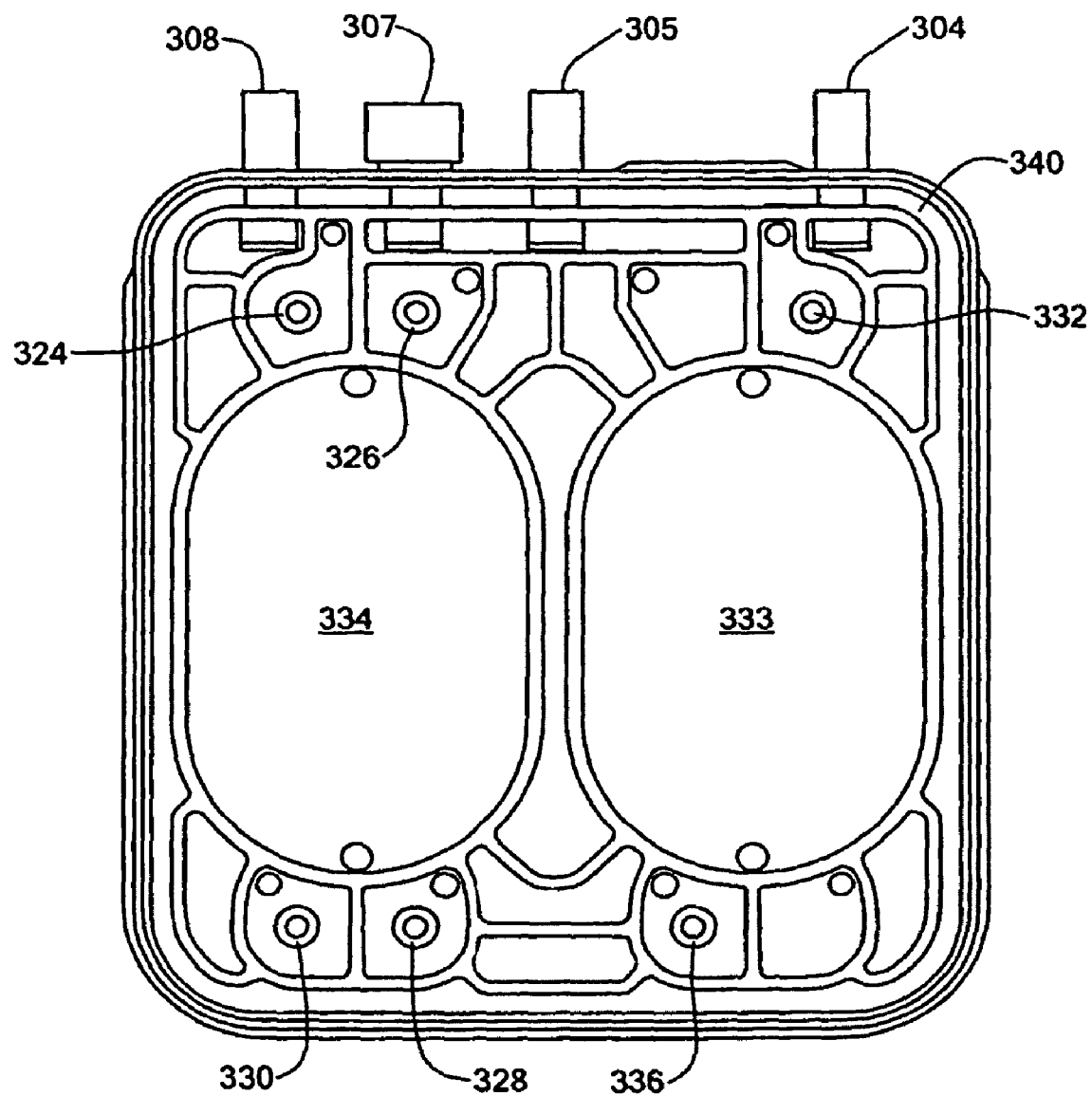
FIG. 7B shows a rear view of the pump cassette in accordance with an embodiment of the present invention.

FIG. 7B shows a rear view of the pump cassette 202 in accordance with an embodiment of the present invention. The rears view of the pump cassette 202 shows various "volcano" valves that are used to open and close various fluid pathways within the pump cassette 202. The valves include an RBC priming valve 326, an RBC valve 328, an incubation bag valve 330, a working solution valve 332, and a working solution connection to RBC line valve 336. The volcano valves and the pumping chambers are all operated pneumatically from the rear of the pump cassette 202, as discussed below.

Blood Pump

As discussed above, each blood pump 104 prepares incubation solution by mixing an anti-pathogen solution with RBCC. A disposable pump cassette 202 is used to handle the various fluids. The pump cassette 202 serves as an interface between the blood pump 104, the RBCC container 106, and the incubation bag 118 so that no working solution, RBCC, or incubation solution comes into actual contact with the components of the blood pump 104. The blood pump 104 preferably uses pneumatics to operate the pump cassette 202 as well as other components, as discussed below.

The blood pump 104 produces the incubation solution by causing working solution to be drawn into the working solution chamber 333 and pumping working solution from the working solution chamber 333 into the channel 310 while drawing RBCC into the RBC chamber 334 through the channel 310. This causes the working solution and RBCC to be mixed within the channel 310 and the RBC chamber 334. The mixture (incubation solution) is pumped from the RBC chamber 334 to the incubation bag 118 through the outlet port 308.

In a typical embodiment of the present invention, the working solution is pumped from the working solution chamber 333 using a pulsing technique in which small quantities of working solution are pumped at predetermined intervals and the pulsing of working solution is adjusted periodically using a closed feedback loop in order to produce an incubation solution having a predetermined concentration of working solution, with predetermined limits. Specifically, the working solution is delivered in a pulsatile mode where the pulse width of the exit valve on the working solution chamber is controlled. The fluid valve is pulsed at a pulse width and interval that is predetermined for each pumping stroke and is adjusted stroke-by-stroke according to the amounts of working solution and RBCC pumped, as described below. The blood pump 104 can support pulse widths above some minimum value, and the interval between pulses is increased in order to achieve an effective pulse width below the minimum value.

The blood pump 104 preferably includes a library of generic pump control (N-Pump) functions. The N-Pump library functions are used to perform various generic pumping operations such as, for example, pumping fluid into a chamber of the pump cassette, pumping fluid out of a chamber of the pump cassette, measuring the amount of fluid pumped, performing air detection, and maintaining tank pressures. The blood pump 104 preferably also includes a Fluid Logic Module (FLM) that contains higher level functions that employ the N-Pump library functions to implement application-specific functions (such as specific logic for mixing the working solution with the RBCC to produce the incubation solution).

The blood pump 104 includes one master board connected to two pump boards that together perform the N-Pump and FLM functions. The master board communicates to each of the pump boards via a multi-drop RS-485 bus. Each pump board controls a single pump chamber of the pump cassette 202 and the valves on its board.

Figure 8:
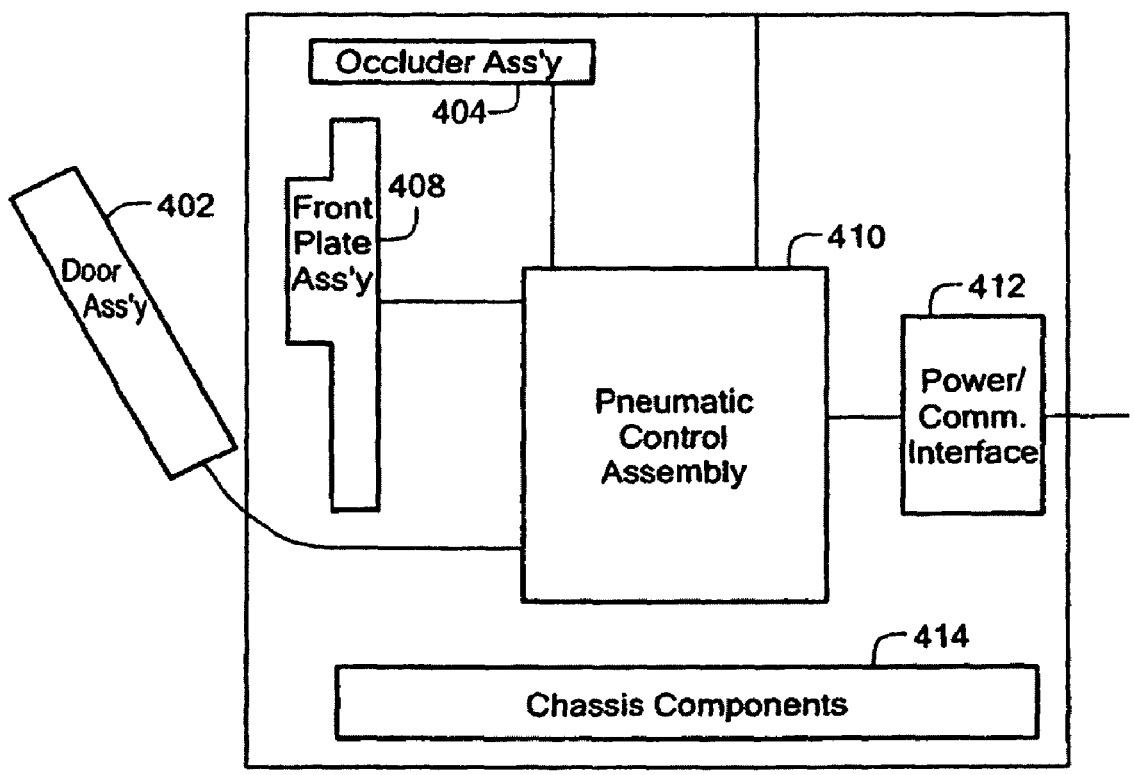
FIG. 8 shows a conceptual block diagram of the blood pump in accordance with an embodiment of the present invention.

FIG. 8 shows a conceptual block diagram of the blood pump 104 in accordance with an embodiment of the present invention. Among other things, the blood pump 104 includes a door assembly 402 as described in above embodiments, an occluder assembly 404, a front plate assembly 408, a pneumatic control assembly 410, a power/communication interface 412 including connectors for the 12-Volt power supply and the RS-232 communication link to the process controller 120, and chassis components 414. Each of these assemblies is discussed below.

Pneumatic Control Assembly

The pneumatic control assembly 410 provides positive and negative air pressure for operating the various other pneumatically controlled components and also acts as the general controller for the blood pump 104. The pneumatic control assembly 410 contains three electromechanical pump module assemblies, namely a tank management module assembly and two chamber module assemblies (one for the working solution pump chamber and one for the RBC pump chamber). Each pump module assembly includes an aluminum manifold, pneumatic valves, pneumatic fittings, a valve interface board, and an electronics board that includes pressure transducers and a dedicated microprocessor. The tank management module assembly handles all communication between the blood pump and the process controller 120, synchronizes pumping of the chamber module assemblies, maintains positive and negative air pressure in various accumulators, seals and unseals the door assembly, engages and disengages the occluders, monitors the door open/closed status, and monitors the air-in-line sensor, as described below. Each chamber management assembly controls a separate one of the pump chambers, and also controls the fluid valves associated with the pump chamber and measures the volume of liquids pumped through the pump chamber.

Figure 9A:
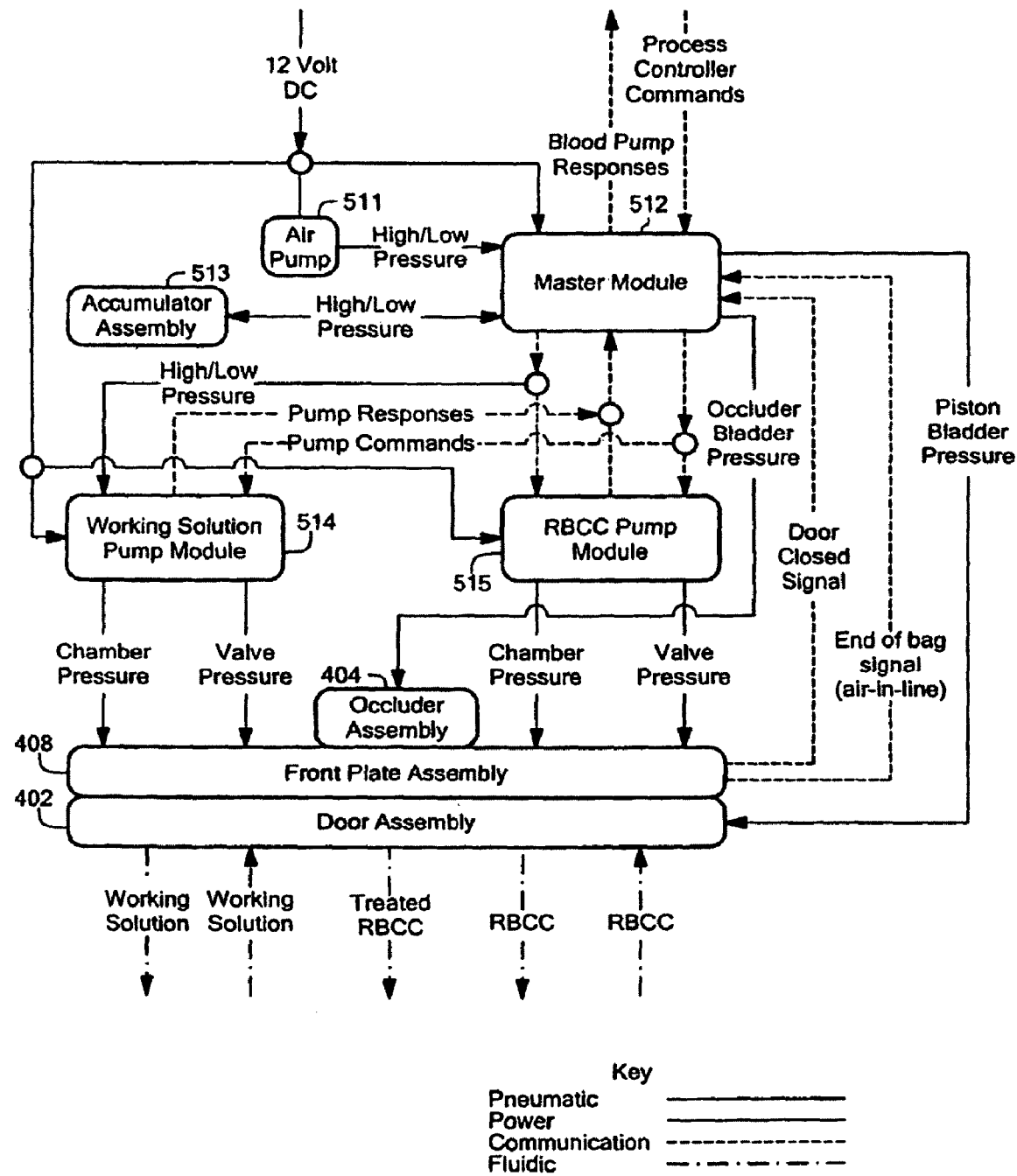
FIG. 9A is an architectural flow diagram showing the relationship between the pneumatic control assembly and the other assemblies in accordance with an embodiment of the present invention.

FIG. 9A is an architectural flow diagram showing the relationship between the pneumatic control assembly 410 and the other assemblies in accordance with an embodiment of the present invention in this figure, the pneumatic control assembly 410 is represented by master module 512, accumulator assembly 513, working solution pump module 514, and RBCC pump module 515. The air pump 511 is considered to be one of the chassis components 414. The air pump 511 generates high and low air pressure for the master module 512, which stores high and low air pressure in the accumulator assembly 513. The pneumatic control assembly 410 directs air pressure (positive and negative) to the various pneumatic mechanisms of the pump. The master module 512 pneumatically controls bladders in the occluder assembly 404 and a bladder in the door assembly 402. The master module 512 provides high and low air pressure to the working solution pump module 514 and the RBCC pump module 515. The working solution pump module 514 controls the working solution chamber 333 and associated valves of the pump cassette 202 through the front plate assembly 408, and the RBCC pump module 515 controls the RBC chamber 334 and associated valves of the pump cassette 202 through the front plate assembly 408, as described below.

Figure 9B:
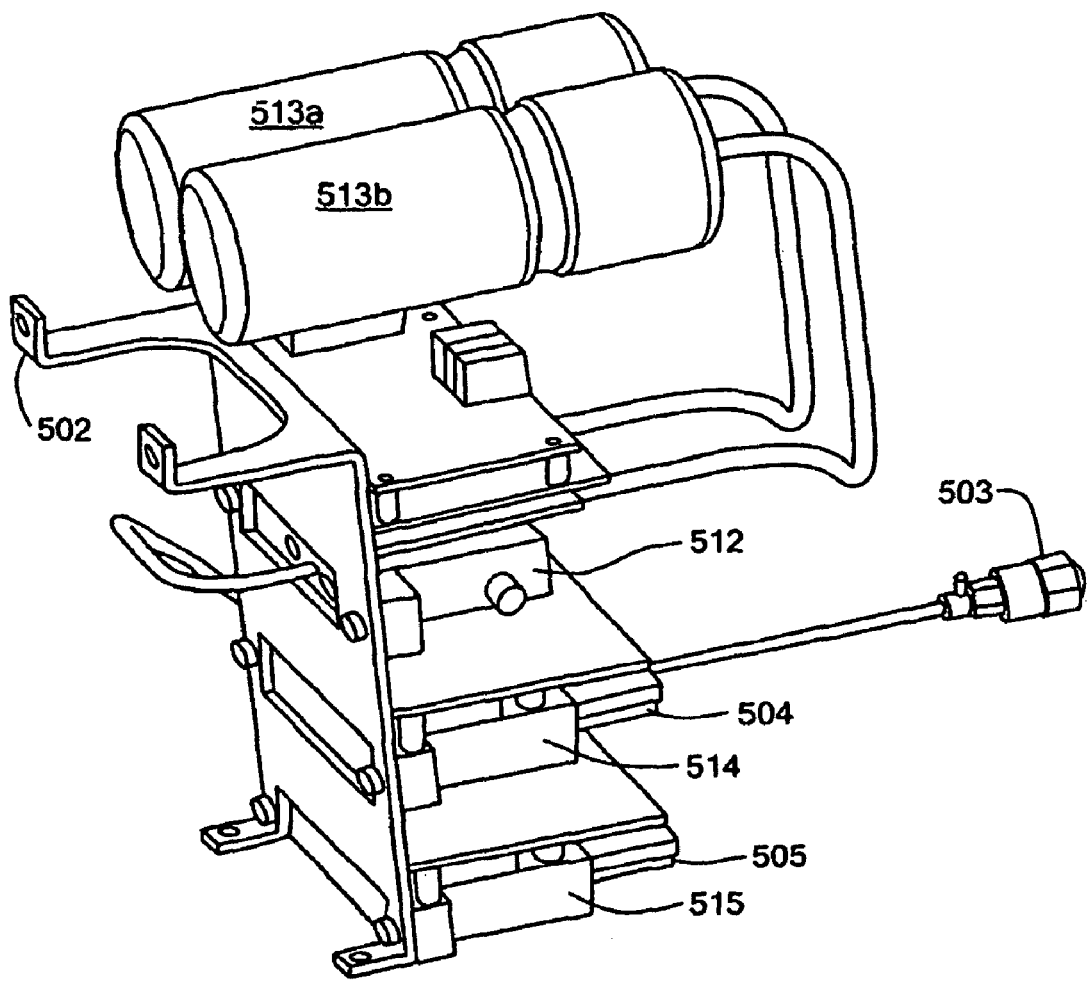
FIG. 9B shows an exemplary embodiment of the pneumatic control assembly in accordance with an embodiment of the present invention.

FIG. 9B shows an exemplary embodiment of the pneumatic control assembly 410 in accordance with an embodiment of the present invention. Among other things, the pneumatic control assembly 410 includes manifold mounting bracket 502, a negative pressure accumulator (pressure bottle) 513a, a positive pressure accumulator (pressure bottle) 513b, a manual door vent mechanism 503, the Tank Management Module Assembly 512, the two Chamber Module Assemblies 514 and 515, and associated tubing and fittings.

The tank management module 512 includes an input/output (I/O) board, a CPU board, a valve-interface board, a pneumatic manifold system, pneumatic valves, pressure transducers 2-vent covers (mufflers), stand-offs, and associated tubing and fittings. The tank management module 512 is used to control the pressures in the accumulators 513, the bladder in the door assembly 402, and bladders in the occluder assembly 404. The I/O board contains electrical controls for controlling LEDs that provide status information to the operator. The pressure transducers are used to monitor the pressures of the accumulators 513 and the bladder in the door assembly 402.

In the un-powered state, the pneumatic valve that controls flow to the bladder in the door assembly 402 preferably shuts closed. This prevents the door from being opened in the event of a loss of power.

In the un-powered state, the pneumatic valves that control flow to the bladders in the occluder assembly 404 are preferably channeled to vent. This causes the occluders to occlude the tubing to prevent further flow of fluid through the tubing, as discussed below.

Each chamber module 514 and 515 includes a CPU board, a valve interface board, pneumatic manifold system, pneumatic valves (including a VSO (variable) valve), a VSX chamber (504 and 505 respectively), O-ring, copper mesh, vent cover (muffler), stand-offs, pressure transducers, and associated tubing and fittings. Each chamber module assembly controls the pneumatics for one of the pumping chambers and its associated valves. The VSX chambers 504 and 505 act as reference volumes in order to measure the volume of fluid that is delivered with the FMS system. The pressure transducers are used to monitor the pressure of the VSX chamber, and of the pumping chamber. The positive pneumatic system contains a pressure relief valve to prevent the air pump from pressurizing the positive system to greater than 16.0 psig.

In the un-powered state, all of the pneumatic valves preferably open the fluid valves to the positive pressure line. This ensures that the fluid valves are closed if there is a loss of power.

The blood pump 104 typically includes three microprocessor systems, one on the tank management module 512 and one on each of the chamber modules 514 and 515. These three microprocessor systems monitor each other for normal operation. Each microprocessor system also monitors key internal processes and data for validity. If any of these monitors fail, a failsafe line permits any of the three processors to stop pumping operations, close all of the fluid valves and occluder, and send an anomaly signal to the process controller. If the blood pump 104 detects an anomaly with the commands received from the process controller (e.g., commands received out of sequence), then the blood pump 104 will stop fluid flow and send an anomaly signal to the process controller.

Front Plate Assembly

The front plate assembly includes all necessary pneumatic pathways to interface to the disposable pump cassette 202. The front plate assembly 408 includes a bezel and a bezel gasket through which the pump cassette 202 is operated. During operation of the blood pump 104, the pump cassette 202 is positioned in the door assembly 402 and is pressed against the front plate assembly 408 in alignment with the bezel and bezel gasket by a bladder in the door assembly 402, as discussed below. Air lines connected to the bezel from the pneumatic control assembly 410 are used to displace membranes of the bezel gasket to operate the various valves and chambers of the pump cassette 202.

Figure 10A:
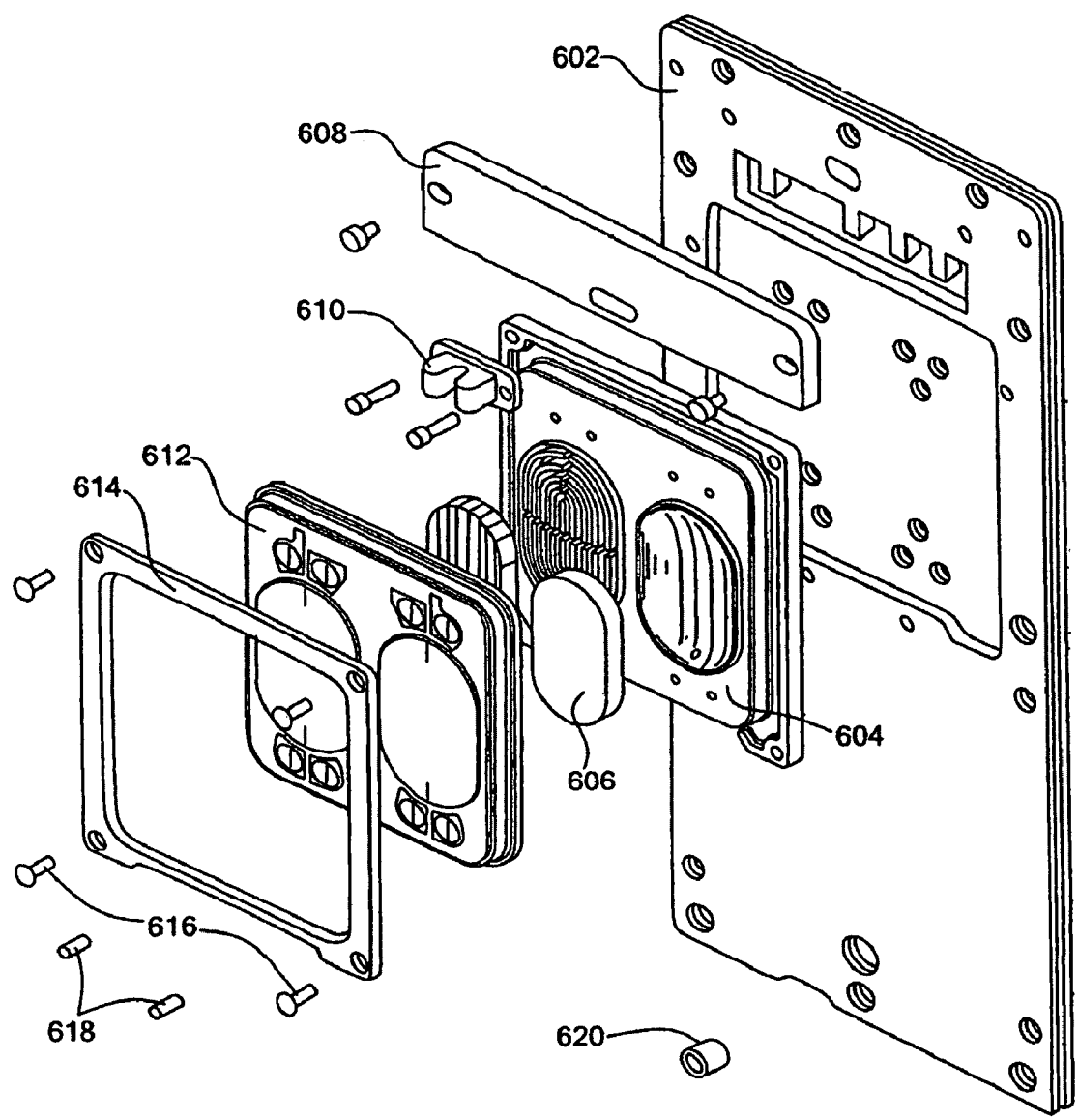
FIG. 10A shows an exploded view of an exemplary front plate assembly in accordance with an embodiment of the present invention.

FIG. 10A shows an exploded view of an exemplary front plate assembly 408 in accordance with an embodiment of the present invention. Among other things, the front plate assembly 408 includes a rigid front plate 602 to which are mounted a bezel 604, chamber foam 606, spacer 608, air-in-line sensor 610, bezel gasket 612, gasket retainer 614, hardware 616, dowel pins 618, and grommet 620. The bezel 604, chamber foam 606, and bezel gasket 612 are mounted to the front plate 602 by the gasket retainer 614 and associated hardware 616, forming a bezel assembly. This bezel assembly is used to control pumping and mixing of fluids using the pump cassette 202, as described below. The front plate 602 includes holes for allowing air tubes to pass between the rear of the bezel 604 and the pneumatic control assembly 410, which is typically situated behind the front plate 602. The front plate 602 also includes openings for occluder blades and for engaging a door latch mechanism, as described below. The air-in-line sensor 610 is positioned so as to align with and engage the RBCC inlet tube 204, and is used during blood processing to detect air in the RBCC inlet tube 204 indicating that there is no more RBCC to be processed.

Figure 10B:
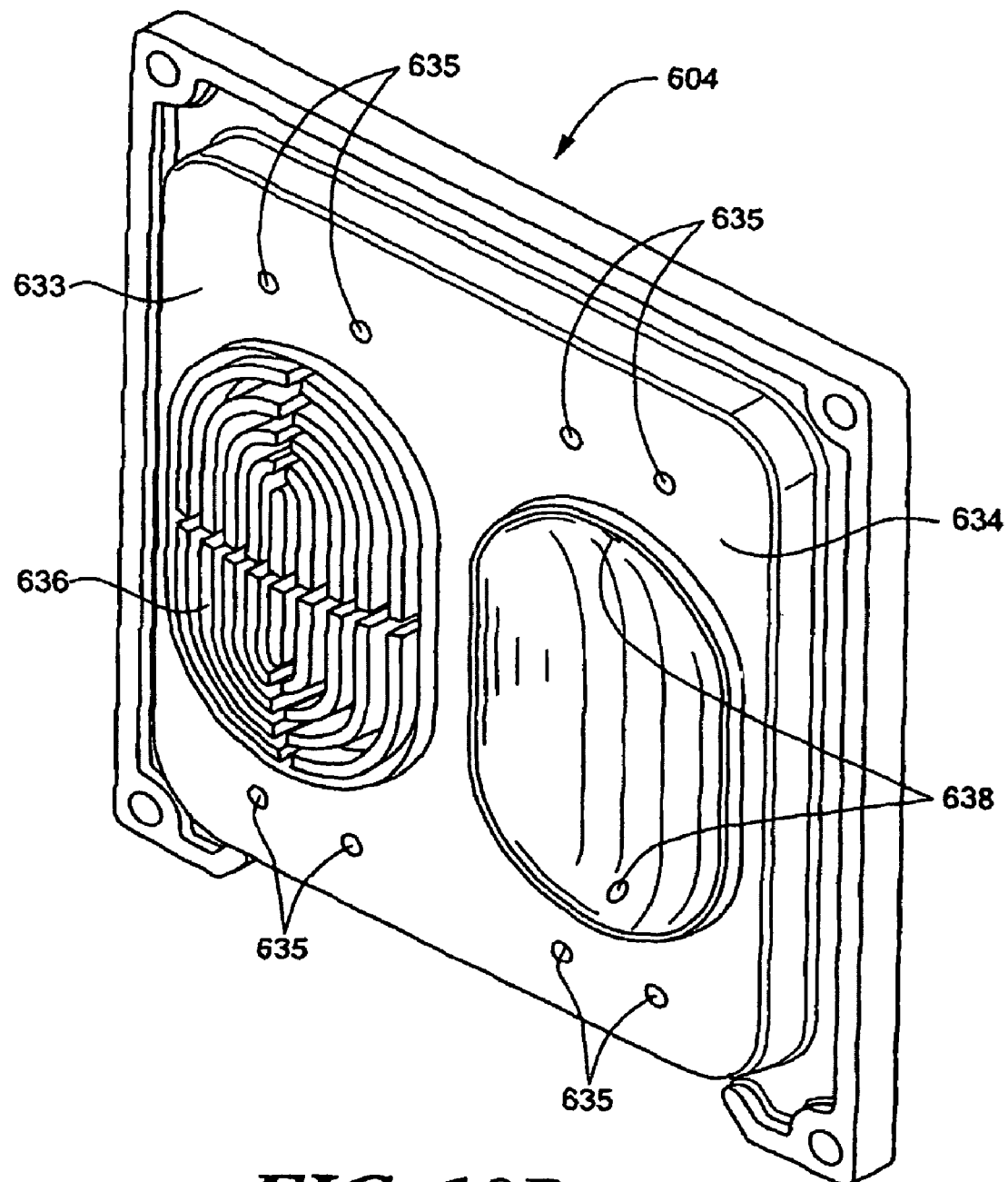
FIG. 10B shows a front view of an exemplary bezel in accordance with an embodiment of the present invention.

FIG. 10B shows a front view of an exemplary bezel 604 in accordance with an embodiment of the present invention. The bezel 604 is preferably a molded polycarbonate/ABS unit including, among other things, a working solution chamber cavity 633 for operating the working solution chamber 333 of the pump cassette 202, an RBC chamber cavity 634 for operating the RBC chamber 334 of the pump cassette 202, and various valve cavities 635 for operating the various valves of the pump cassette 202. The working solution chamber cavity 633 is preferably molded with rib structures 636 that allow for airflow within the working solution chamber cavity 633 but mechanically restrict the amount of working solution that can be drawn into the working solution chamber 333 of the pump cassette 202. The compounder 102 preferably uses the same molded bezel 604 as the blood pump 104, but with the rib structures 636 removed (e.g., by precision machining) to allow for greater pumping capacity. The bezel is described in greater detail in Application D75.

Figure 10C:
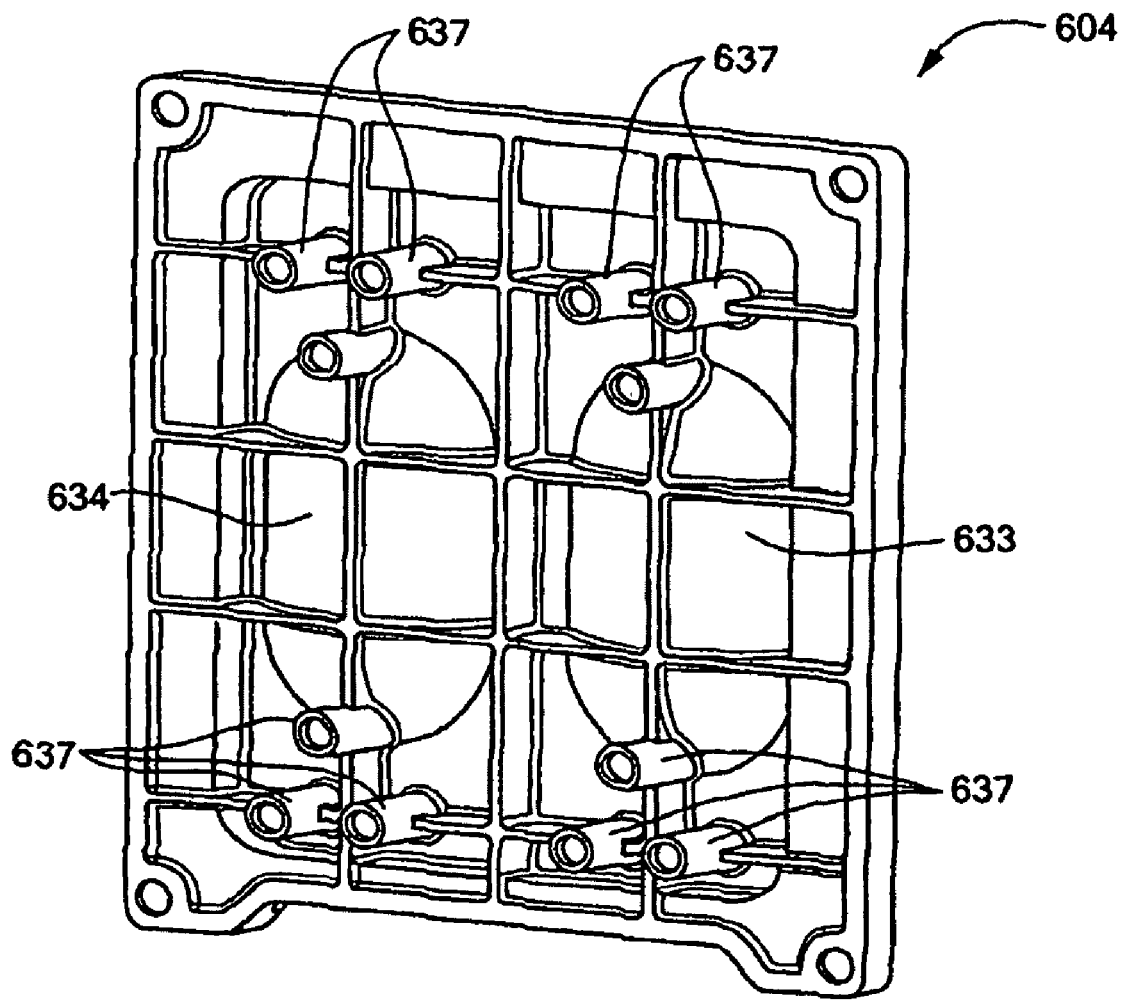
FIG. 10C shows a rear view of an exemplary bezel in accordance with an embodiment of the present invention.

FIG. 10C shows a rear view of the bezel 604 in accordance with an embodiment of the present invention. The bezel 604 includes integral solvent bondable tubing connections (ports) 637 to which pneumatic tubing from the pneumatic control assembly 410 are connected. In this embodiment, each of the valve cavities 635 is associated with a single integral port 637, and each of the chamber cavities 633 and 634 are associated with two integral ports 637. The integral ports 637 allow the pneumatic connections to be made without independent fittings and accompanying O-rings.

Figure 10E:
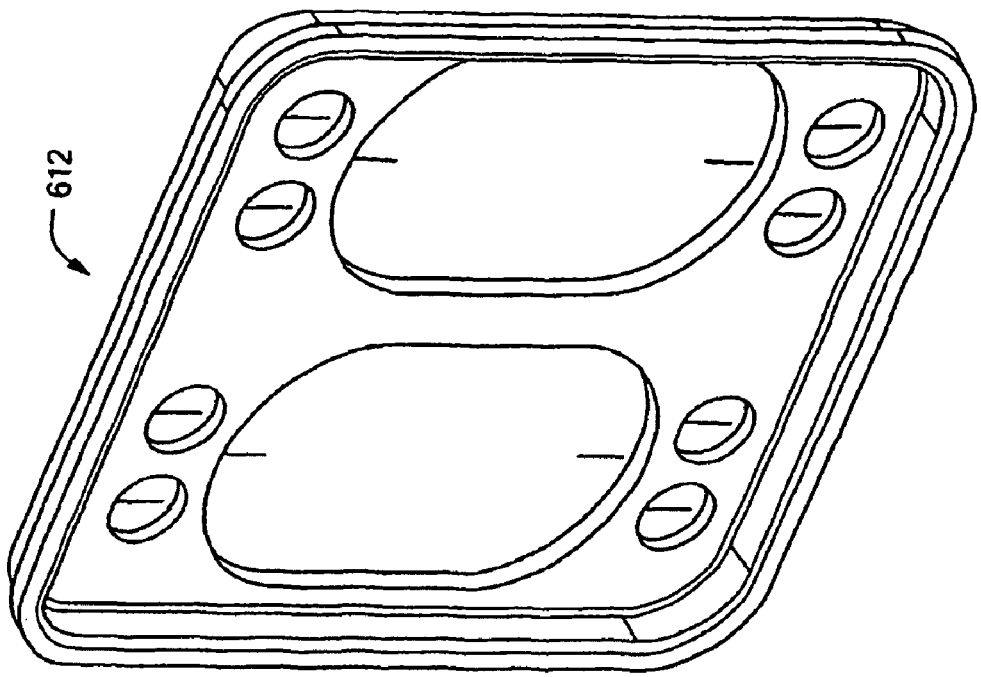
FIG. 10E shows a rear view of an exemplary bezel gasket in accordance with an embodiment of the present invention.
Figure 10D:
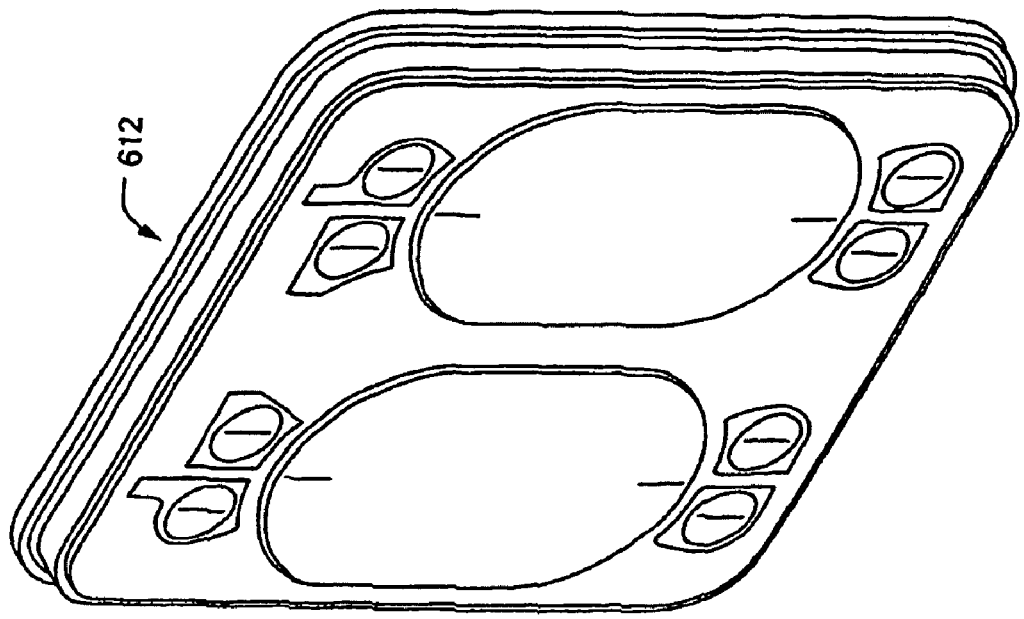
FIG. 10D shows a front view of an exemplary bezel gasket in accordance with an embodiment of the present invention.

FIG. 10D shows a front view of an exemplary bezel gasket 612 in accordance with an embodiment of the present invention. The bezel gasket 612 fits over the front of the bezel 604 and acts as an interface between the bezel 604 and the pump cassette 202 for sealing the fluid paths of the pump cassette 202 and for actuating the chambers and valves of the pump cassette 202. The pump cassette 202 is pressed firmly against the front side of the bezel gasket 612 during blood processing in order to produce an air-tight seal between the bezel gasket 612 and the pump cassette 202. The bezel gasket 612 includes membranes that correspond to the chamber cavities and valve cavities. Positive and negative air pressure produced through the bezel cavities operate on the bezel gasket membranes, which in turn operate on the chambers and valves of the pump cassette 202.

FIG. 10E shows a rear view of an exemplary bezel gasket 612 in accordance with an embodiment of the present invention. The rear side of the bezel gasket 612 contacts the front side of the bezel 604, and is pressed firmly against the bezel 604 during blood processing in order to produce an air-tight seal. The bezel gasket 612 includes membranes that correspond to the chamber cavities and valve cavities. Positive and negative air pressure produced through the bezel cavities operate on the bezel gasket membranes, which in turn operate on the chambers and valves of the pump cassette 202.

Door Assembly

The door assembly 402 mounts to the front plate assembly 408, and provides a means to load and align the disposable pump cassette 202 in a cassette receptacle 704 within the blood pump 104. The door assembly 402 provides a force on the pump cassette 202 against the bezel assembly of the front plate assembly 408 in order to provide sealing of the cassette's fluid paths and valves, as described in greater detail in Application D73. The door assembly 402 also provides a surface for the occluders to function against, as described below.

Referring back to FIG. 3A, the door assembly 402 is designed to permit single-handed operation, specifically by pulling up on the handle. However, the door latch 703 is designed, similar to above-described embodiments, so that the door cannot be easily opened when the pump cassette 202 is in place in the cassette receptacle 704 with the door closed and the piston assembly 711 is inflated. Specifically, the latch portions of the door latch 703 have undercuts that engage with recesses in the front plate assembly 408. When the pump cassette is in place in the cassette receptacle 704 with the door closed and the piston assembly 711 is inflated so as to push the pump cassette 202 against the bezel assembly of the front plate assembly 408, a sufficient force is generated between the door assembly 402 and the front plate assembly 408 to prevent the door handle from being easily lifted.

Occluder Assembly

The occluder assembly 404 mounts to the back of the front plate assembly 408, and is used to selectively occlude the RBCC inlet tube 204, the incubation solution outlet tube 206, and the working solution distribution tube 212 as needed for testing, blood processing, and protection in the event of a failure. In the blood pump 104, the occluder assembly 404 includes two occluders, one operating on both the RBCC inlet tube 204 and the incubation solution outlet tube 206, and the other operating on the working solution distribution tube 212. The occluders are controlled pneumatically, and can be controlled independently.

In a typical embodiment of the present invention, each occluder includes an occluder blade that is operated by a flat spring and an inflatable bladder. The occluder blade is coupled to one end of the spring. When the bladder is deflated, the spring extends the occluder blade into an occluding position, which blocks the passage of fluid through the tube(s). When the bladder is inflated, the bladder bends the spring so as to retract the occluder blade from the occluding position, which enables the passage of fluid through the tube(s). In the event of a loss of pneumatics, the occluder defaults to the occluded position so as to prevent fluid from passing through the tubing.

Figure 11:
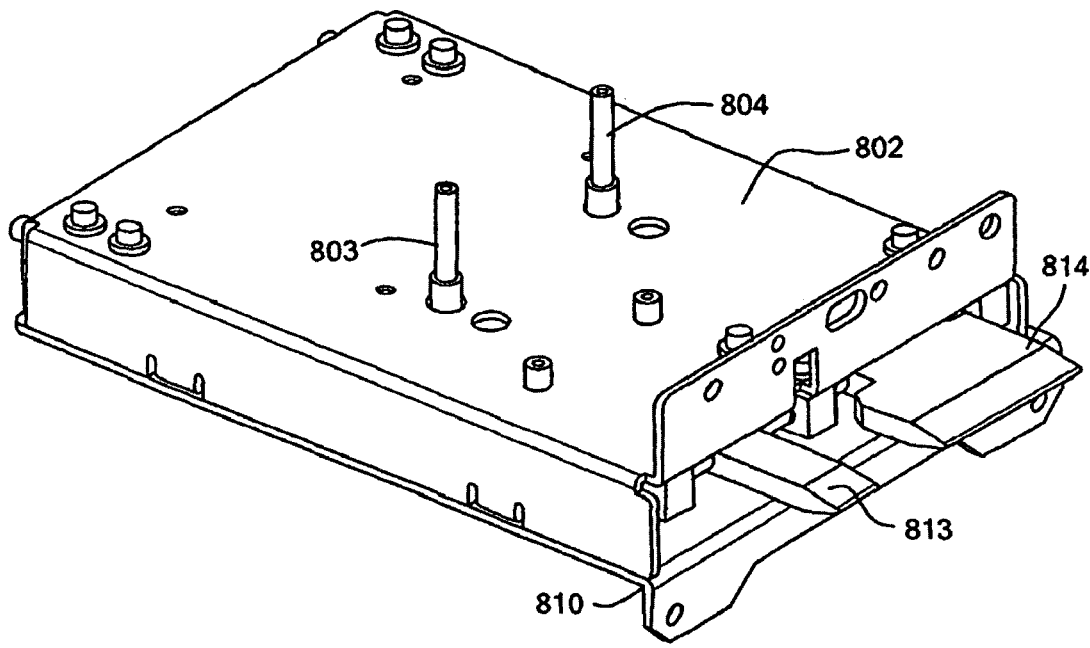
FIG. 11 shows a side perspective view of the occluder assembly in accordance with an embodiment of the present invention.

FIG. 11 shows a side perspective view of the occluder assembly 404 in accordance with an embodiment of the present invention. The occluder assembly 404 includes, among other things, a bottom housing 801, a top housing 802, a first occluder having an occluder blade 813 and other components operated pneumatically through tube 803, and a second occluder having an occluder blade 814 and other components operated pneumatically through tube 804. The occluder assembly 404 is mounted to the front plate assembly 408, with the occluder blades 813 and 814 protruding through slots in the front plate assembly 804. The tubes 803 and 804 are connected to the pneumatic control assembly 410.

Figure 12:
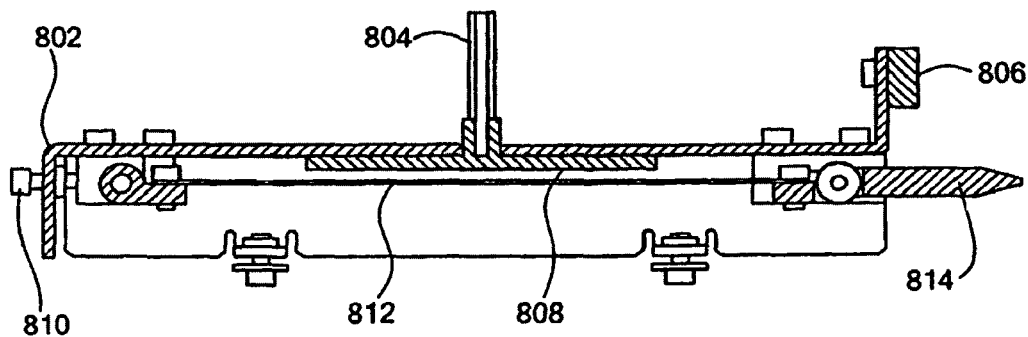
FIG. 12 shows a cross-sectional view of an occluder in accordance with an embodiment of the present invention.

FIG. 12 shows a cross-sectional view of an occluder in accordance with an embodiment of the present invention. Among other things, the occluder includes a flat occluder spring 812 having a rear end coupled to the top housing 802 and a front end coupled to the occluder blade 814, a bladder 808 situated between the top housing 802 and the spring 812, the tube 804 coupled to the bladder 808, and an adjuster 810 for adjusting the protrusion of the occluder blade 814. When the bladder 808 is inflated, the occluder spring 812 is deflected downward at the middle so as to shorten the effective length of the occluder spring 812 and retract the occluder blade 814. When the bladder 808 is deflated, the occluder spring 812 extends flat and therefore extends the occluder blade 814. The occluder blade 814 moves within guides (not shown) that allow the spring to extend and retract the occluder blade 814.

Figure 13:
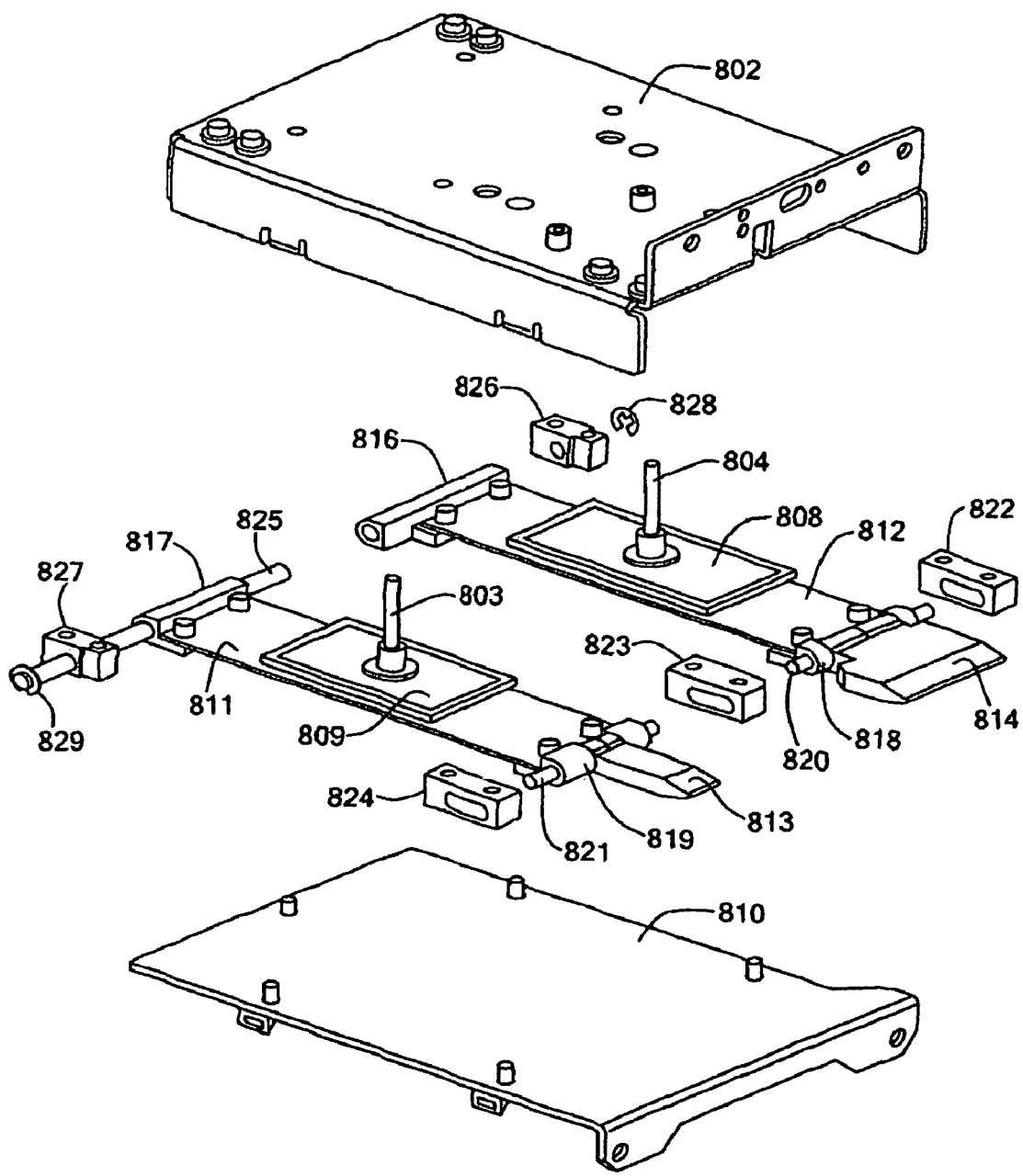
FIG. 13 shows an exploded view of the occluder assembly in accordance with an embodiment of the present invention.

FIG. 13 shows an exploded view of the occluder assembly 404 in accordance with an embodiment of the present invention. Among other things, the occluder assembly 404 includes enclosure top 802, enclosure bottom 810, a first occluder including an occluder blade 813, a shaft 821, a front bracket 819, a rear bracket 817, a bladder 809, and a tube 803, and a second occluder including an occluder blade 814, a shaft 820, a front bracket 818, a rear bracket 816, a bladder 808, and a tube 804. The rear brackets 816 and 817 are mounted to the enclosure top 802 via shaft 825, blocks 826 and 827, and clamps 828 and 829. The rear brackets 816 and 817 are held in a substantially fixed position, although the rear brackets 816 and 817 are able to rotate about the shaft 825 as needed for operation of the occluders. The front bracket 819 is mounted to the enclosure top 802 via shaft 821 and sliding blocks 823 and 824, while the front bracket 818 is mounted to the enclosure top 802 via shaft 820 and sliding blocks 822 and 823. The front brackets 818 and 819 are able to slide forward and backward along channels formed in the sliding blocks 822, 823, and 824 as needed for operation of the occluders. The occluder blades 813 and 814 can be manually retracted if necessary. The edge of the occluder blades 813 and 814 that engages the tubing are typically rounded so as not to cut or crease the tubing.

Chassis Components

The chassis components 414 include various mechanical hardware components that are not considered part of the other assemblies. Among other things, the chassis components 414 include the DC air pump 511, a chassis base, a door sensor (and cable), mounting foot grommets, skins (housing), and associated hardware and fasteners. The housing includes a mounting point, on the back of the unit, for the manual piston bladder (door) vent 503.

Pump Cassette Handling

Referring back to FIG. 1, the pump cassette 202 is installed in the blood pump 104 in accordance with an embodiment of the present invention. Particularly, the pump cassette 202 is installed in the cassette receptacle 704. The door assembly 402 will only close if the pump cassette 202 is oriented correctly in the cassette receptacle 704, and will not close if the pump cassette 202 is inserted backwards so that the tubing connected to the pump cassette 202 does not align with corresponding channels in the door latch 703. When the door assembly 402 is closed and the bladder in the door assembly 402 is inflated, the pump cassette 202 is pressed tightly against the bezel gasket 612 and gasket retainer 614 on the front panel assembly 408, preventing the door assembly 402 from being opened. Additionally, the RBCC inlet tube 204 is captured by the air-in-line sensor 610 on the front plate assembly 408, the occluder blade 813 aligns with and occludes the working solution distribution tube 212, and the occluder blade 814 aligns with and occludes both the RBCC inlet tube 204 and the incubation solution outlet tube 206.

Door Locking/Unlocking

Figure 14:
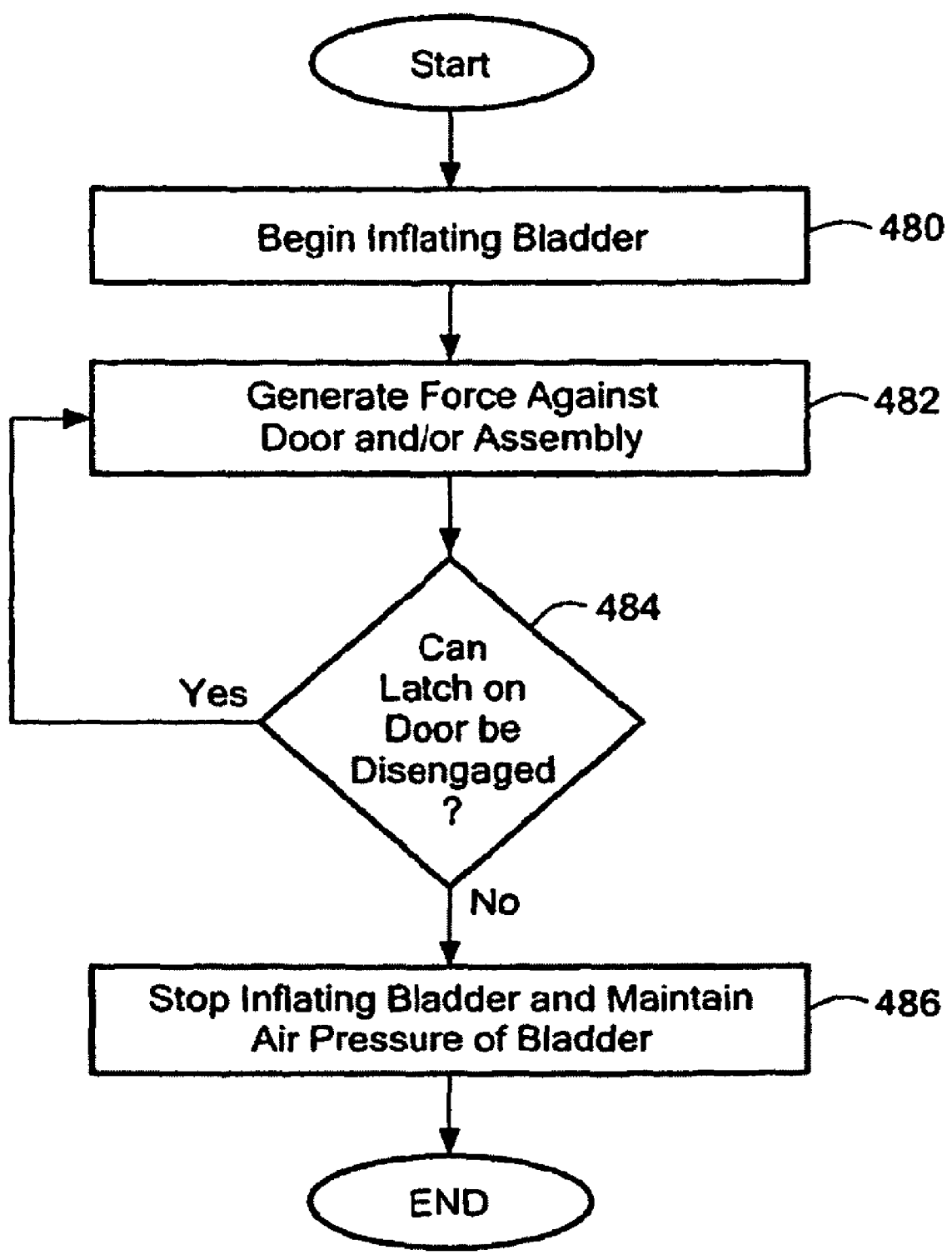
FIG. 14 is a process flow diagram describing a process for locking the door using an inflatable bladder, in accordance with an embodiment of the invention.

FIG. 14 shows a process for locking the door 402 using the inflatable bladder 707, in accordance with one embodiment of the invention. The process begins by inflating the bladder 707, in block 480. Positive pressure is supplied to the bladder 707 via the pneumatic circuit 730, which is precisely controlled by the control unit 751. The control unit 751 may start inflating the bladder 707 based on a wide variety of safety and procedural interlocks. These interlocks may be based, for example, on a signal received from a sensor, such as the door 402 being closed, and/or on an operator input, such as an input from an operator interface indicating a pumping procedure is ready to begin.

The process continues with the bladder 711 generating a force against at least one of the assembly 104 and the door 402, in block 482. Inflating the bladder 707 causes the membrane 732 of the bladder piston 711 to protrude through the frame 708. As inflation continues, the membrane 732 contacts the door 402 and/or assembly 104, generating a force directed at pushing the door 402 (i.e., the back plate 705) and assembly 104 apart. This, in turn, presses the aligned first and second engagement surfaces 220 and 221 tightly together, preventing disengagement of the latch member 703 and thus locking the door 402.

In various embodiments, the membrane 732 may advantageously contact another element instead of, or in combination with, the door 402 and assembly 104. For example, a pump cassette may be positioned between the membrane 732 and the at least one of the door 402 or assembly 104. The membrane 732 pressing on the pump cassette forces the pump cassette against the door 402 or assembly 104, generating a force directed at pushing apart the door 402 and assembly 101. Consequently, similar to the above-described embodiment, the first and second engagement surfaces 220 and 221 are pressed firmly together, locking the door 402.

The control unit 751 continues to inflate the bladder 711 until a force is generated on the at least one of the door 402 and assembly 104 to sufficiently prevent an operator from disengaging the latch member 703, block 484. In various embodiments, the air pressure of the bladder 711 that is required to ensure locking of the door 401 is a predetermined value. The control unit 751 controls the pneumatic circuit 730 to stop inflating the bladder 711 when the predetermined value is met, and maintains the bladder's air pressure at the predetermined value, block 486. Thus, a constant force is applied on the at least one of the door 402 and the assembly 104, keeping the door 401 locked.

To unlock the door 402, the control unit 751 controls the pneumatic circuit 730 to deflate the bladder 711. This causes the piston 711 to move away from the door 402 and/or assembly 104 (or other element), allowing sufficient play between the engagement surfaces 220 and 221 such that the latch member 703 can be disengaged from the assembly 104. In other words, the piston 711 no longer generates a sufficiently large locking force against the noted elements. Consequently, the two surfaces 220 and 221 can disengage from one another.

Manual Teardown

During normal blood pump teardown, the blood pump 104 receives commands from the process controller 120 to release pressure against the pump door so that the door can be opened by the operator. The pressure against the door comes from both the door piston bladder and the occluders. While the door piston bladder is pressurized and the tubing occluders are engaged, it is virtually impossible for the operator to open the pump door and remove the pump cassette. If communication between the process controller 120 and the blood pump 104 is lost, then the operator will need to relieve this pressure manually in order to remove the cassette. Among other things, this involves the operator pressing the manual door release valve on the back of the pump to deflate the bladder in the door assembly. The operator may also manually retract the occluders if necessary.

It should also be noted that the flow diagrams are used herein to demonstrate various aspects of the invention, and should not be construed to limit the present invention to any particular flow or implementation. In some cases, certain process steps can be omitted or performed in a different order than shown without changing the overall results or otherwise departing from the true scope of the invention.

The present invention may be embodied in other specific forms without departing from the true scope of the invention. The described embodiments are to be considered in all respects only as illustrative and not restrictive.

What is claimed is:

1. A door locking system comprising:
   an assembly facing an inside surface of an attached door, and including a latching structure, the latching structure defining a recess facing away from the inside surface of the door when the door is in a closed position;
   a force-generating member coupled to the door for applying a force against the assembly to urge the door to an open position; and
   a latch member movably connected to the door for engagement with the latching structure to keep the door closed, the latch member comprising:
   a distal coupling element adapted and configured to fit within the recess of the latching structure; and
   a proximal connecting element adapted and configured to connect to a handle on the door, wherein actuation of the handle moves the distal coupling element into or out of alignment with the latching structure;
   wherein
   application of the force creates an engagement force between the latching structure of the assembly and the latch member of the door to keep the door latched, and release of the force decreases the engagement force, allowing disengagement of the latch member from the latching structure when the handle is actuated.

2. The door locking system of claim 1, wherein the force-generating member is coupled to the inside surface of the door, and the force is applied between the inside surface of the door and a cassette within the assembly.

3. The door locking system of claim 2, wherein the force-generating member comprises a piston for applying a force against the cassette.

4. The door locking system of claim 3, wherein the force-generating member further comprises an expandable bladder acting on the piston.

5. The door locking system of claim 2, wherein the cassette comprises a pump cassette.

6. The door locking system of claim 1, wherein the latch member is under an elastic force urging the distal latching end into alignment with the latching structure.

7. The door locking system of claim 6, wherein the elastic force is provided by a spring.

8. A door locking system comprising:
   an assembly facing an inside surface of an attached door, and including a latching structure;
   a force-generating member coupled to the door for applying a force against the assembly to urge the door to an open position; and
   a latch member movably connected to the door for engagement with the latching structure to keep the door closed, the latch member comprising:
   a distal coupling element defining a recess facing the inside surface of the door, a component of the latching structure being adapted and configured to fit within the recess of the latch member; and
   a proximal connecting element adapted and configured to connect to a handle on the door, wherein actuation of the handle moves the distal coupling element into or out of alignment with the latching structure;
   wherein
   application of the force creates an engagement force between the latching structure of the assembly and the latch member of the door to keep the door latched, and release of the force decreases the engagement force, allowing disengagement of the latch member from the latching structure when the handle is actuated.

9. The door locking system of claim 8, wherein the force-generating member is coupled to the inside surface of the door, and the force is applied between the inside surface of the door and a cassette within the assembly.

10. The door locking system of claim 9, wherein the force-generating member comprises a piston for applying a force against the cassette.

11. The door locking system of claim 10, wherein the force-generating member further comprises an expandable bladder acting on the piston.

12. The door locking system of claim 9, wherein the cassette comprises a pump cassette.

13. The door locking system of claim 8, wherein the latch member is under an elastic force urging the distal latching end into alignment with the latching structure.

14. The door locking system of claim 13, wherein the elastic force is provided by a spring.

* * * * *